(12) United States Patent
Yang et al.

(10) Patent No.: US 10,730,898 B2
(45) Date of Patent: Aug. 4, 2020

(54) COMPOUND AND USE THEREOF AND PLATINUM COMPLEX AND LIPIDOSOME THEREOF

(71) Applicants: SHENYANG PHARMACEUTICAL UNIVERSITY, Shenyang (CN); BEIJING SNOWLE BIO-TECH CO., LTD., Beijing (CN)

(72) Inventors: Li Yang, Shenyang (CN); Qun Zeng, Beijing (CN); Juan Song, Shenyang (CN)

(73) Assignees: SHEYANG PHARMACEUTICAL UNIVERSITY, Shenyang (CN); BEIJING SNOWLE BIO-TECH CO., LTD., Beijing (CN)

( * ) Notice: Subject to any disclaimer, the term of this patent is extended or adjusted under 35 U.S.C. 154(b) by 0 days.

(21) Appl. No.: 16/072,614

(22) PCT Filed: Jan. 13, 2017

(86) PCT No.: PCT/CN2017/071114
§ 371 (c)(1),
(2) Date: Jul. 25, 2018

(87) PCT Pub. No.: WO2017/128963
PCT Pub. Date: Aug. 3, 2017

(65) Prior Publication Data
US 2019/0031696 A1    Jan. 31, 2019

(30) Foreign Application Priority Data
Jan. 25, 2016   (CN) .......................... 2016 1 0049404

(51) Int. Cl.
| | | |
|---|---|---|
| C07F 15/00 | (2006.01) | |
| A61K 31/282 | (2006.01) | |
| A61P 35/00 | (2006.01) | |
| A61K 9/127 | (2006.01) | |

(52) U.S. Cl.
CPC .......... *C07F 15/0093* (2013.01); *A61K 9/127* (2013.01); *A61K 31/282* (2013.01); *A61P 35/00* (2018.01)

(58) Field of Classification Search
None
See application file for complete search history.

(56) References Cited

U.S. PATENT DOCUMENTS

| | | |
|---|---|---|
| 2,790,779 A | 4/1957 | Spivack et al. |
| 2,850,387 A | 9/1958 | Town |
| 5,047,535 A | 9/1991 | Lahav et al. |
| 2002/0120096 A1 | 8/2002 | Tsuchida et al. |
| 2006/0222696 A1 | 10/2006 | Okada et al. |
| 2010/0197890 A1 | 8/2010 | McTavish |
| 2015/0045428 A1 | 2/2015 | Sengupta et al. |

FOREIGN PATENT DOCUMENTS

| | | |
|---|---|---|
| CN | 104744563 | 7/2015 |
| EP | 0185225 A1 | 6/1986 |
| EP | 0255718 A2 | 2/1988 |
| JP | S61-171496 A | 8/1986 |
| JP | S61-249993 A | 11/1986 |
| JP | H03-200795 A | 9/1991 |
| JP | 2008-538105 A | 10/2008 |
| JP | 2012-516330 A | 7/2012 |
| WO | WO 2003/006007 A1 | 1/2003 |
| WO | WO 2013/103707 A1 | 7/2013 |
| WO | WO 2014/201376 | 12/2014 |

OTHER PUBLICATIONS

Sallay et al., Helvetica Chimica Acta (1954), 37, pp. 778-785.*
CAS SciFinder English language abstract (database CAPLUS Acc. No. 1955:32103) of Helvetica Chimica Acta (1954), 37, pp. 778-785, retrieved Dec. 8, 2019.*
English summary of Office Communication issued in Chinese Patent Application No. 201610049404.9, dated Sep. 11, 2018.
Gianasi et al., "HPMA copolymers platinates containing dicarboxylato ligands. Preparation, characterization and in vitro and in vivo evaluation," *Journal of Drug Targeting*, 10(7):549-556, 2002.
Oberoi et al., "Nanocarriers for delivery of platinum anticancer drugs," *Adv. Drug Deliv. Rev.*, 65(0):1667-1685, 2013.
Popovitz-Biro et al., "A new series of amphiphilic molecules forming stable Z-type (polar) Langmuir-Blodgett films," *J. Am. Chem. Soc.*, 112:2498-2506, 1990.
Uchino et al., "Cisplatin-incorporating polymeric micelles (NC-6004) can reduce nephrotoxicity and neurotoxicity of cisplatin in rats," *British Journal of Cancer*, 93:678-687, 2005.
Zhu et al., "Regulation of the chiral twist and supramolecular chirality in co-assemblies of amphiphilic $_L$-glutamic acid with bipyridines," *Chem. Eur. J.*, 17:3429-3437, 2011.
English translation of International Search Report issued in International Application No. PCT/CN2017/071114, dated Mar. 23, 2017.
Itoh et al., "Infrared reflection absorption and sum frequency generation spectroscopic study on the structures of the LB films of palmitoyl-L- and DL-ornithine and palmitoyl-L- and DL-lysine," *Vibrational Spectroscopy*, 29(1 and 2):197-203, 2002.
Song et al., "3-octadecylcarbamoylacrylic acid-cisplatin nanocomplexes for the development of novel liposome formulation," *Drug Delivery*, 23(9):3285-3293, 2016.
English translation of Office Communication issued in Japanese Patent Application No. 2018-557176, dated May 9, 2019.
Appleton et al., "Reaction of the cis-diamminediaquaplatinum(II) cation with N-acetylglycine," *Inorg. Chem.*, 28:815-819, 1989.

(Continued)

*Primary Examiner* — Brian J Davis
(74) *Attorney, Agent, or Firm* — Parker Highlander PLLC

(57) ABSTRACT

Provided are a platinum complex and a liposome thereof, and a use thereof. The platinum complex contains a carboxyl group having pH sensitivity, wherein in a comparatively low pH environment (such as in tumour tissues), the carboxyl group is liable to deprotonate, facilitating an improvement in the drug release inside tumour tissues and improving the therapeutic effect of drugs. In addition, the platinum complex can be well combined with the membrane materials of lipidosomes, so as to improve the encapsulation ratio and drug loading capacity of lipidosomes. Experiments indicate that the lipidosomes of the platinum complex can reduce the toxic and side effects of drugs and increase the therapeutic effect thereof.

10 Claims, 12 Drawing Sheets

(56) References Cited

OTHER PUBLICATIONS

Extended European Search Report issued in European Patent Application No. 17743578.1, dated Sep. 19, 2019.
Li et al., "The effect of lipocisplatin on cisplatin efficacy and nephrotoxicity in malignant breast cancer treatment," *Biomaterials*, 35(24):6462-6472, 2014.

* cited by examiner

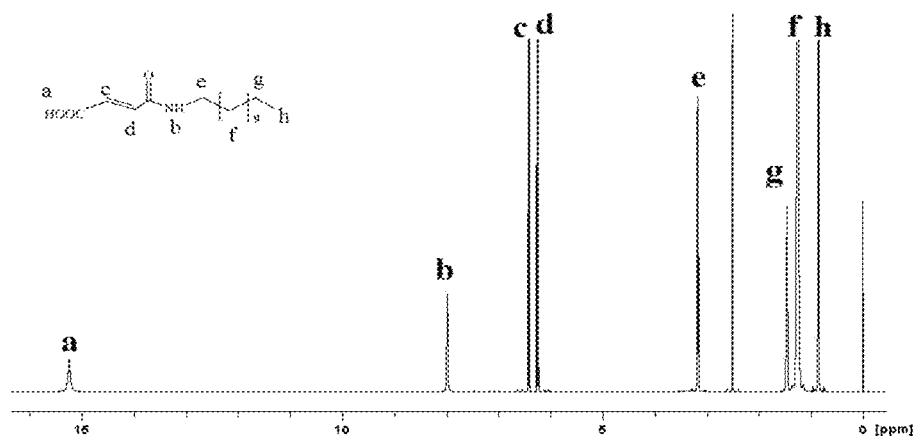
Figure 1-a
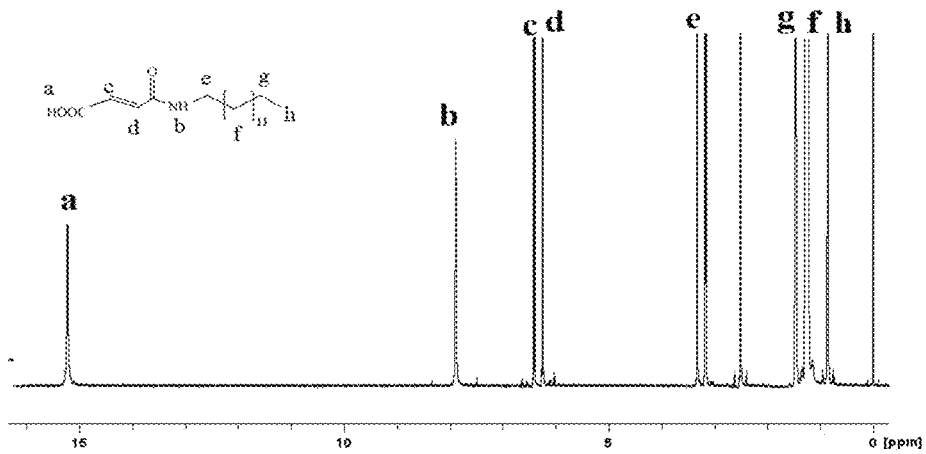
Figure 1-b

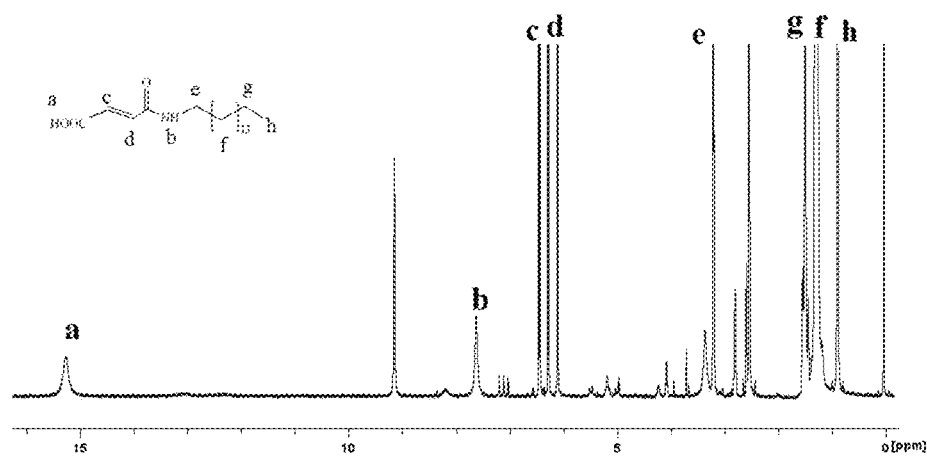
Figure 1-c
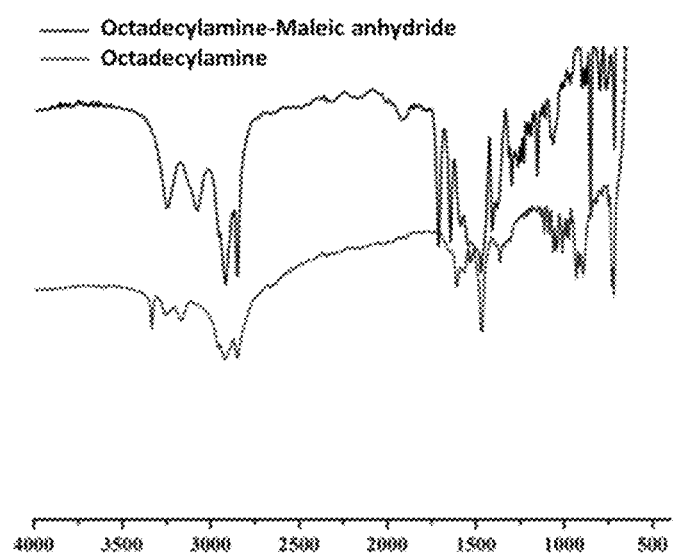
Figure 1-d-1

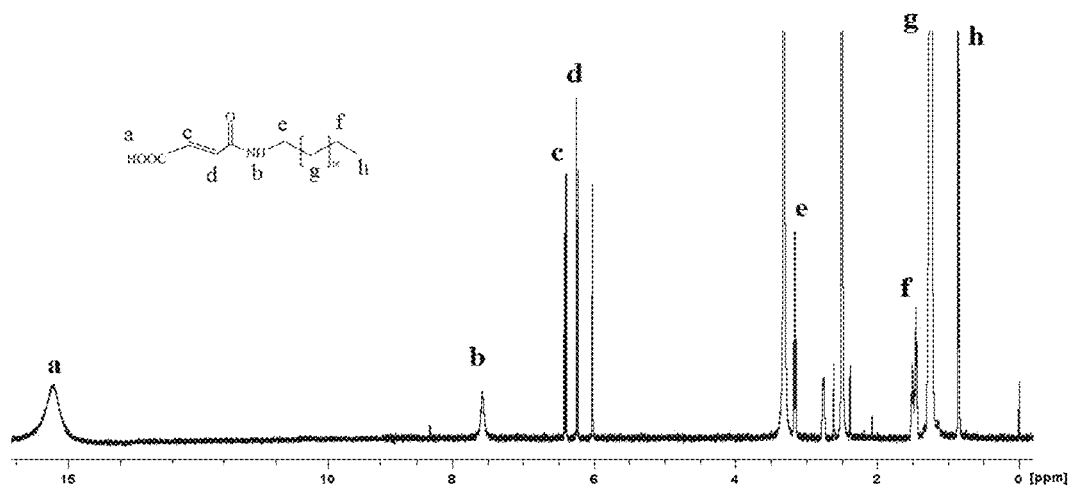
Figure 1-d-2
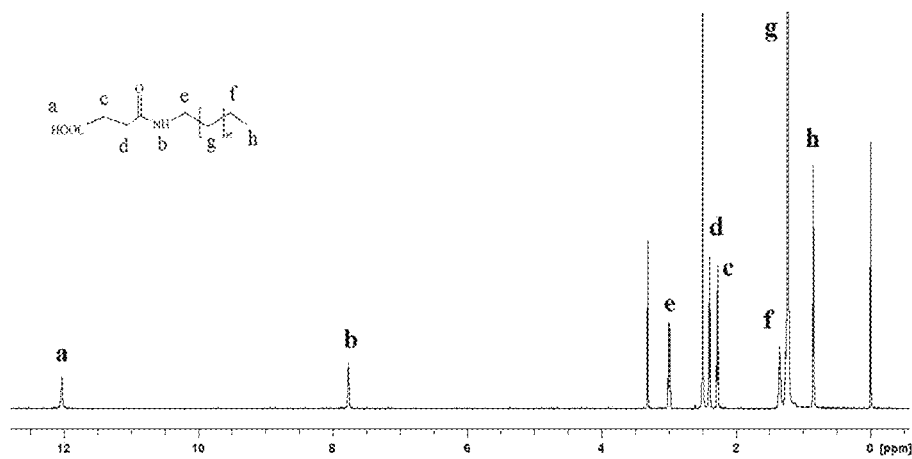
Figure 1-e

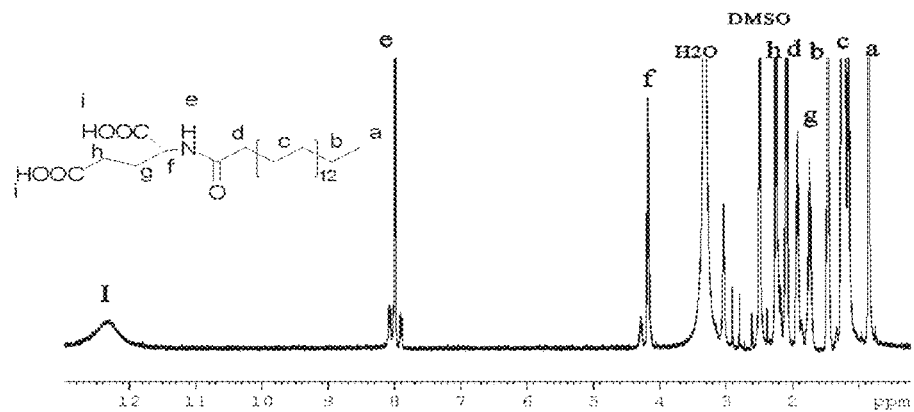
Figure 1-f
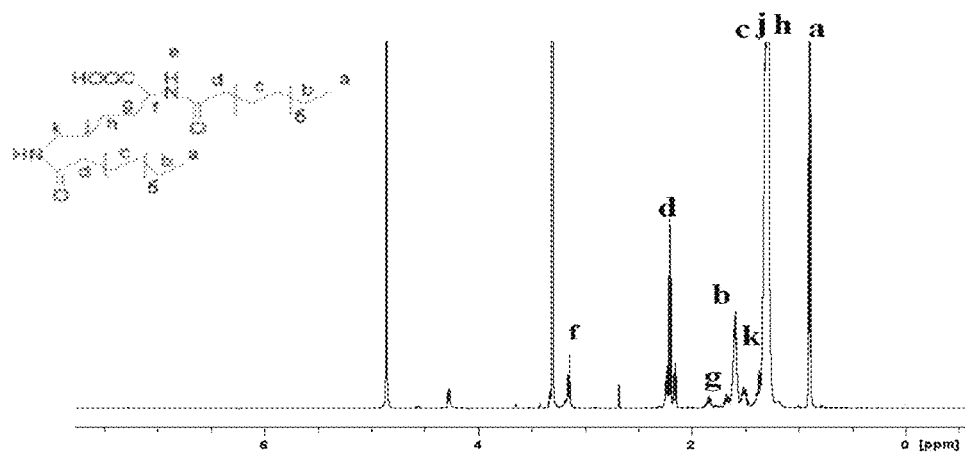
Figure 1-g

Figure 1-h

COMPOUND AND USE THEREOF AND PLATINUM COMPLEX AND LIPIDOSOME THEREOF

CROSS REFERENCE TO RELATED APPLICATIONS

The present application is a national phase application under 35 U.S.C. § 371 of International Application No. PCT/CN2017/071114, filed Jan. 13, 2017, which claims priority to Chinese Patent Application No. 201610049404.9, entitled "COMPOUND AND USE THEREOF AND PLATINUM COMPLEX AND LIPIDOSOME THEREOF", filed on Jan. 25, 2016 with the State Intellectual Property Office of People's Republic of China, which are incorporated herein by reference in their entirety.

FIELD

The present invention relates to the field of pharmaceuticals, and in particular to a compound and use thereof, and a platinum complex and liposome thereof.

BACKGROUND

Since American scientist B. Rosenborg accidentally discovered that cisplatin has antitumor activity in 1965, the synthesis, application and research of platinum-based anticancer drugs have been developed rapidly. As compared with traditional cytotoxic antitumor drugs, platinum-based anti-tumor drugs have a unique mechanism of action, which mainly targets DNA. Platinum-based anti-tumor drugs are hydrolyzed after entering into cells to form positively charged platinum hydrates with high activity, which react with nucleic acid and protein to form a DNA intrastrand and/or interstrand conjugate, thereby resulting in a change in the secondary structure of DNA, hindering the transcription and replication of DNA and eventually leading to apoptosis. At present, cis-dichlorodiamine platinum (i.e., Cisplatin), cis-1,1-cyclobutane dicarboxylic acid diamine platinum (i.e., Carboplatin), cis-oxalic acid-(trans-(–)-1,2-cyclohexanediamine)platinum (i.e., Oxaliplatin), Nedaplatin, Eptaplatin, Lobaplatin, and the like, have been successfully developed. Platinum-based anti-tumor drugs have characteristics such as wide anti-cancer spectrum, strong activity, no cross tolerance. There is statistical data showing that in 70% to 80% of all chemotherapy regimens, platinums are dominated, or involved in composition. However, platinum-based anti-cancer drugs lack specificity for tumor cells. After intravenous injection, they are quickly eliminated in the blood and rapidly distributed into various organ tissues, especially liver, kidney, intestine and other tissues, thereby resulting in severe toxic side effects which mainly include nephrotoxicity, digestive tract toxicity (nausea, vomiting), bone marrow toxicity, neurotoxicity and ototoxicity, and the like. Moreover, it has disadvantages, for example, the drug reaches the tumor site at a relatively low concentration, reducing its efficacy; and long-term administration will also cause tolerance in cancer cells, thereby reducing the chemotherapeutic effect.

In order to solve the above problems, it is necessary to prolong the circulation time of the drug in the blood and reduce non-specific binding between drugs and proteins, thereby reducing the systemic toxic side effects and improving the pharmaceutical efficacy. Pharmaceutical researchers in many countries have devoted themselves to the study on the targeting delivery system of platinum-based drugs, such as micelles, vesicles, liposomes, and nanoparticles. These drug carriers can effectively entrap the drug therein for delivery and control the release of the drug by taking advantage of the properties of carriers, thereby increasing the effective accumulation of the drug at the target site and reducing the concentration thereof in non-lesion sites, which can both improve the therapeutic efficacy and reduce the systemic side effects.

In the prior art, many methods for developing a platinum-based preparation by entrapping the drug in a carrier have been disclosed. For example, Uchino et al., have prepared a micelle with a drug loading of 30 wt. % (NC-6004) by complexing cisplatin with carboxyl group-rich polyethylene glycol-b-polyglutamic acid, which has entered into phase II clinical trials [British Journal of Cancer (2005) 93, 678-687]. However, since the resulting micelle is formed by cross-linking between the side chains of polyamino acids, the lyophilized powders of the complex obtained by this method is very difficult to re-dissolve after freeze-drying and the efficacy of the preparation is not improved. Access Pharmaceuticals prepared AP5280 by combining the commonly used polymer HPMA with cisplatin, which has an accumulation at tumor sites 19 times of the cisplatin injection and significantly reduced the nephrotoxicity of cisplatin [J. Drug Target 10 (2002) 549-556]. These studies have shown that platinum compounds can bind to macromolecules through chemical bonds sensitive to environment, thereby effectively reducing the toxicity of platinum-based drugs and improving the therapeutic efficacy thereof. Moreover, the chemical bonds sensitive to environment are critical to the pharmaceutical efficacy of platinum-based anticancer drugs, because they can change the hydration rate of platinum compounds in vivo. The faster platinum compounds are hydrated in vivo, the stronger the antitumor effect thereof is, and however at the same time, the higher the toxicity thereof is. Poulomi Sengupta et al. showed that the pharmaceutical effect produced by combing cisplatin with cholesterol-maleic anhydride via monocarboxylato and O→Pt bond is significantly superior to that of the complex formed by combining cisplatin with macromolecules via stable dicarboxylato bond, and however a greater toxicity may be produced therefrom. To this end, researchers try to prepare platinum-based anti-tumor drugs into liposomes in order to change the distribution of drugs in vivo, reduce adverse reactions and expand the scope of application.

However, platinum-based anti-tumor drugs are very difficult to be prepared into liposomes. Taking cisplatin as an example, there are two major problems in the preparation of liposomes thereof. Firstly, cisplatin has solubility in water of about 1 mg/mL at 4° C. Secondly, cisplatin can only be prepared into liposomes by passive loading, and thus pH gradient active loading cannot be performed by reference to the marketed doxorubicin liposome Doxil and the like. The above two reasons usually lead to a low drug loading of cisplatin liposomes. The cisplatin long-circulating liposome (SPI-077) developed by ALAZA, is a PEGylated liposome, which increases the solubility of cisplatin mainly by heating. In the preparation of SPI-077, hydration is performed at a high temperature of 65° C., allowing an increase in the solubility of cisplatin by about 8 mg/mL. However, the cisplatin long-circulating liposome prepared by this method still has a very low drug loading. For SPI-077, the drug can only be released by degrading the lipid bilayer by lipase. Therefore, there are few free drugs to be released from liposomes and enter into the extracellular fluid of the tumor cells, thereby leading to a decrease in antitumor activity [Advanced Drug Delivery Reviews, 2013, 65(13-14): 1667-1685].

It follows that, the existing techniques still cannot solve the above-mentioned problems of platinum compounds, and cannot improve the drug loading while maintaining a good activity of the drug and moreover reducing toxic side effects thereof.

SUMMARY

In view of this, the technical problem to be solved by the present invention is to provide a compound and use thereof, and a platinum complex and liposome thereof. The compound provided by the present invention can be used for the preparation of a platinum complex, and the liposome prepared from the platinum complex not only significantly increases the anti-tumor activity thereof, but also significantly reduce the toxicity thereof, especially the nephrotoxicity. Moreover, the obtained platinum complex liposome has a high encapsulation ratio and drug loading, a simple preparation process, and a value for industrial application.

The present invention provides a platinum complex having a structure represented by formulas I-a or I-b:

Formula I-a

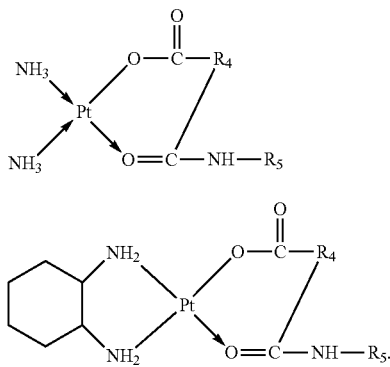

Formula I-b

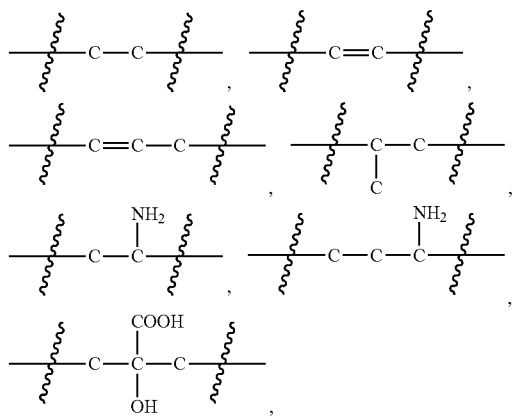

and hyaluronic acid with two carboxyl groups removed; and $R_5$ is selected from $-C_cH_{2c+1}$, with $c=12\sim18$.

The present invention further provides a platinum complex having a structure represented by formulas I-c or I-d:

Formula I-c

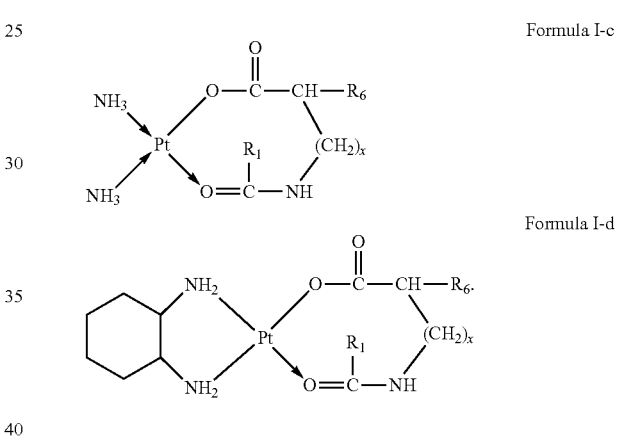

Formula I-d $R_4$ is selected from the group consisting of $-C_bH_{2b}-$, $-C_bH_{2b-2}-$, $-Ar-C_bH_{2b}-$, $-Ar-C_bH_{2b-2}-$, $-Ar-O-C_bH_{2b}-$, $-Ar-O-C_bH_{2b-2}-$, and hyaluronic acid with two carboxyl groups removed, with $b=0\sim22$;

$R_5$ is selected from the group consisting of $-H$, $-C_cH_{2c+1}$, $-C_cH_{2c-1}$, $-Ar-C_cH_{2c+1}$, $-Ar-C_cH_{2c-1}$, $-Ar-O-C_cH_{2c+1}$, $-Ar-O-C_cH_{2c-1}$, and chitosan with one amino group removed, with $c=1\sim22$;

wherein H attached to any C can be substituted with a substituent; and wherein the substituent is one or more of $-NH_2$, $-OH$, $-COOH$, halogen and $-Ar$.

In an embodiment of the present invention, $R_4$ is selected from the group consisting of $-C_bH_{2b}-$, $-C_bH_{2b-2}-$, and hyaluronic acid with two carboxyl groups removed, with $b=1\sim10$; and $R_5$ is selected from the group consisting of $-C_cH_{2c+1}$, $-C_cH_{2c-1}$, and chitosan with one amino group removed, with $c=8\sim18$.

In an embodiment of the present invention, $R_4$ is selected from the group consisting of $-CH_2-$, $-C-C-$, $-C=C-$, $-C=C-C-$, $-C-C-$ with branch C, $-C-C-$ with $NH_2$, $-C-C-C-$ with $NH_2$, $-C-C-C-$ with COOH and OH, and hyaluronic acid with two carboxyl groups removed; and $R_5$ is selected from $-C_cH_{2c+1}$, with $c=12\sim18$.

The present invention further provides a platinum complex having a structure represented by formulas I-c or I-d:

$R_1$ is selected from the group consisting of $-H$, $-C_nH_{2n+1}$, $-C_nH_{2n-1}$, $-Ar-C_nH_{2n+1}$, $-Ar-C_nH_{2n-1}$, $-Ar-O-C_nH_{2n+1}$, and $-Ar-O-C_nH_{2n-1}$, with $n=1\sim22$;

$R_6$ is selected from the group consisting of $-NH_2$, $-NH-CO-(CH_2)_eCH_3$, $-(CH_2)_dNH-CO-(CH_2)_e CH_3$, $-C_dH_{2d}-NH_2$, $-C_dH_{2d-2}-NH_2$, $-C_dH_{2d}-COOH$, and $-C_dH_{2d-2}-COOH$, with $d=1\sim8$ and $e=1\sim21$; $x=0\sim10$;

wherein H attached to any C can be substituted with a substituent; and wherein the substituent is one or more of $-NH_2$, $-OH$, $-COOH$, halogen and $-Ar$.

In an embodiment of the present invention, $x=0\sim10$;

$R_1$ is selected from the group consisting of $-H$, $-C_nH_{2n+1}$, and $-C_nH_{2n-1}$, with $n=8\sim20$;

$R_6$ is selected from the group consisting of $-NH_2$, $-NH-CO-(CH_2)_eCH_3$, $-C_dH_{2d}-NH_2$, $-C_dH_{2d-2}-COOH$, and $-(CH_2)_dNH-CO-(CH_2)_eCH_3$, with $d=1\sim6$ and $e=8\sim20$.

In an embodiment of the present invention, $x=0\sim6$;

$R_1$ is $-C_nH_{2n+1}$, with $n=8\sim18$;

$R_6$ is selected from the group consisting of $-NH_2$, $-(CH_2)_2-COOH$, $-NH-CO-(CH_2)_eCH_3$, and $-(CH_2)_4NH-CO-(CH_2)_{14}CH_3$.

In some embodiments, x=0; $R_1$ is —$C_nH_{2n+1}$, with n=8~18; and $R_6$ is —$(CH_2)_2$—COOH, —$(CH_2)_4NH_2$, or —$(CH_2)_4NH$—CO—$(CH_2)_{14}CH_3$.

In some embodiments, x=1~6; $R_1$ is —$C_nH_{2n+1}$, with n=8~18; and $R_6$ is —$NH_2$.

The present invention provides an amphiphilic compound having a structure represented by Formula II:

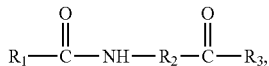

Formula II wherein:

$R_1$ is selected from the group consisting of —H, —$C_nH_{2n+1}$, —$C_nH_{2n-1}$, —Ar—$C_nH_{2n+1}$, —Ar—$C_nH_{2n-1}$, —Ar—O—$C_nH_{2n+1}$, and —Ar—O—$C_nH_{2n-1}$, with n=1~22;

$R_2$ is selected from the group consisting of —$C_mH_{2m}$—, —$C_mH_{2m-2}$—, —$C_mH_{2m}$—NH—, and —$C_mH_{2m-2}$—NH—, with m=1~8;

$R_3$ is selected from the group consisting of —OH, —$C_aH_{2a+1}$, —$C_aH_{2a-1}$, —Ar—$C_aH_{2a+1}$, —Ar—$C_aH_{2a-1}$, —Ar—O—$C_aH_{2a+1}$, and —Ar—O—$C_aH_{2a-1}$, with a=1~22;

wherein H attached to any C can be substituted with a substituent;

wherein the substituent is one or more of —$NH_2$, —OH, —COOH, halogen and —Ar; and $R_2$ and $R_3$ comprise in structure at least one —COOH.

In the amphiphilic compound provided by the present invention:

$R_1$ is —$C_nH_{2n+1}$, $R_2$ is

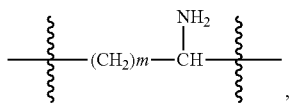

and $R_3$ is —OH;

or $R_1$ is —$C_nH_{2n+1}$, $R_2$ is

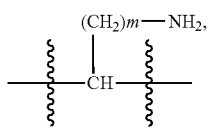

and $R_3$ is —OH;

or $R_1$ is —$C_nH_{2n+1}$, $R_2$ is

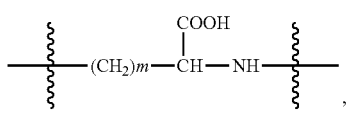

and $R_3$ is —$C_aH_{2a+1}$;

or $R_1$ is —$C_nH_{2n+1}$, $R_2$ is

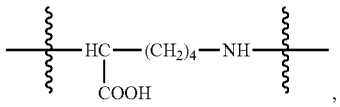

and $R_3$ is —$C_aH_{2a+1}$;

wherein n=8~18, m=2~6, and a=8~18.

The amphiphilic compound provided by the present invention has a structure represented by formulas II-a or II-b:

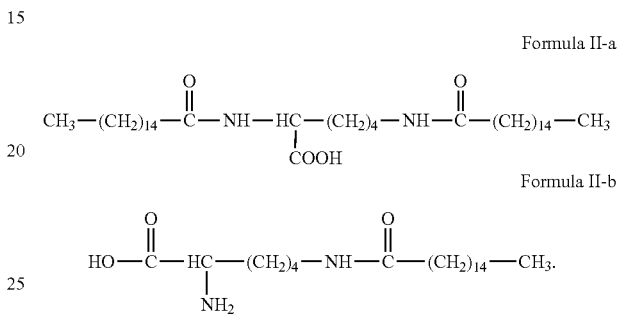

The platinum complex provided by the present invention is prepared by forming coordination bonds between a platinum compound such as cisplatin, carboplatin, oxaliplatin, nedaplatin or lobaplatin (but not limited to such platinum-based drugs) and the carboxyl and amide groups in an amphiphilic compound. In the present invention, the reaction condition is not specially limited, as long as it is a reaction condition well known in the art for use in preparing such a platinum complex.

The amphiphilic compound used in the platinum complexes of the formulas I-a and I-b of the present invention can be prepared by amidation reaction between one carboxyl group of a dibasic acid (anhydride) and an aliphatic amine; there is no limitation for the reaction and it can be any synthesis reaction generating the structure. The amphiphilic compound used in the platinum complexes of the formulas I-c and Id of the present invention can be prepared by amidation reaction between fatty acyl chloride and an amino acid (such as glutamic acid, aspartic acid, lysine, but not limited thereto, and any compound with a similar structure can be used). In the present invention, the reaction condition is not specially limited, as long as it is a reaction condition well known in the art for use in preparing amide by reacting amine and acid, amine and acyl chloride.

The present invention further provides a platinum complex liposome, comprising the platinum complex provided by the present invention, a lipid membrane material and/or a stabilizer, wherein the ratio between the platinum complex and the lipid membrane material is (99:1) to (1:99).

The ratio is on a mass, molar or volume basis.

In the liposome provided by the present invention, the lipid membrane material comprises a composition of phospholipid and/or cholesterol, wherein the lipid membrane material comprises 1-100 parts phospholipid and 0-60 parts cholesterol by mass.

In the liposome provided by the present invention, the phospholipid is any one or a composition of two or more of egg-yolk lecithin, soy lecithin, hydrogenated soya phospholipid, phosphatidylserine, phosphatidylinositol, phosphatidylethanolamine, phosphatidylglycerol, dilauroylphosphatidylcholine, dimyristoylphosphatidylcholine, dipalmitoylphosphatidylcholine, distearoylphosphatidylcholine dioleoylphosphatidylcholine, dilauroylphosphatidylglycerol, dimyristoylphosphatidylglycerol, dipalmitoylphosphatidylglycerol, distearoylphosphatidylglycerol, dioleoylphosphatidylglycerol, phosphoglycerol, dierucoylphosphatidylglycerol, PEGylated phospholipid, and the like.

The present invention provides a medicament for the treatment of cancers, comprising the liposome provided herein.

The platinum complex and liposome thereof provided by the present invention can further be prepared into a different existing dosage form by adding a suitable adjuvant and an additive by techniques well known in the art, such as injection, freeze-dried powder for injection; liposome suspension, tablet, gel, implant, available for administration via intravenous injection, local injection, implantation, inhalation, oral administration, and the like.

The present invention provides a compound having a structure represented by Formula II with a good biocompatibility, wherein the carboxyl and amide groups are capable of complexing with a platinum-based drug to form unstable coordination bonds, which can increase the hydration rate of the drug in vivo and thereby improving the pharmaceutical effect thereof. At the same time, the platinum complex prepared from the compound provided by the present invention can bind to the membrane material of the liposome well, thereby improving the encapsulation ratio and drug loading of the liposome. In addition, the platinum complex prepared from the compound provided by the present invention has a carboxyl group and thus is pH-sensitive, wherein in the environment with a low pH (such as tumor tissue), the carboxyl group tends to be deprotonated, which is favorable for promoting the release of the drug in the tumor tissue and improving the therapeutic effect thereof. It is shown through experiments that the liposome provided by the present invention can reduce the toxic side effects of a drug and improve the therapeutic effect thereof.

BRIEF DESCRIPTION OF THE DRAWINGS

FIG. 1-*a* shows the nuclear magnetic resonance spectrum of the amphiphilic compound of Example 1;

FIG. 1-*b* shows the nuclear magnetic resonance spectrum of the amphiphilic compound of Example 2;

FIG. 1-*c* shows the nuclear magnetic resonance spectrum of the amphiphilic compound of Example 3;

FIG. 1-*d*-1 shows the infrared spectrum of the amphiphilic compound of Example 4;

FIG. 1-*d*-2 shows the nuclear magnetic resonance spectrum of the amphiphilic compound of Example 4;

FIG. 1-*e* shows the nuclear magnetic resonance spectrum of the amphiphilic compound of Example 5;

FIG. 1-*f* shows the nuclear magnetic resonance spectrum of the amphiphilic compound of Example 9;

FIG. 1-*g* shows the nuclear magnetic resonance spectrum of the amphiphilic compound of Example 10;

FIG. 1-*h* shows the nuclear magnetic resonance spectrum of the amphiphilic compound of Example 11;

FIG. 2-1*b* shows the infrared spectrum of the platinum complex of Example 13;

FIG. 2-2*a* shows the infrared spectrum of the platinum complex of Example 14;

FIG. 2-2*b* shows the infrared spectrum of the platinum complex of Example 15;

FIG. 2-3*a* shows the infrared spectrum of the platinum complex of Example 16;

FIG. 2-3*b* shows the infrared spectrum of the platinum complex of Example 17;

FIG. 2-4*a* shows the infrared spectrum of the platinum complex of Example 18;

FIG. 2-4*b* shows the infrared spectrum of the platinum complex of Example 19;

FIG. 2-5*a* shows the infrared spectrum of the platinum complex of Example 20;

FIG. 2-5*b* shows the infrared spectrum of the platinum complex of Example 21;

FIG. 2-6*a* shows the infrared spectrum of the platinum complex of Example 22;

FIG. 2-7*a* shows the detected infrared spectrum of the platinum complex of Example 23;

FIG. 2-7*b* shows the infrared spectrum of the platinum complex of Example 24;

FIG. 2-8*a* shows the infrared spectrum of the platinum complex of Example 25;

FIG. 2-9*a* shows the infrared spectrum of the platinum complex of Example 26;

FIG. 2-9*b* shows the infrared spectrum of the platinum complex of Example 27;

FIG. 3 shows an electron microscopy image of the liposome prepared in Example 31;

FIG. 4 shows the particle size distribution of the liposome prepared in Example 31;

FIG. 5 shows the change in body weight in mice after drug administration (10 mg/kg); and FIG. 6 shows the survival rate of mice.

DETAILED DESCRIPTION OF EMBODIMENTS

Figure 2:
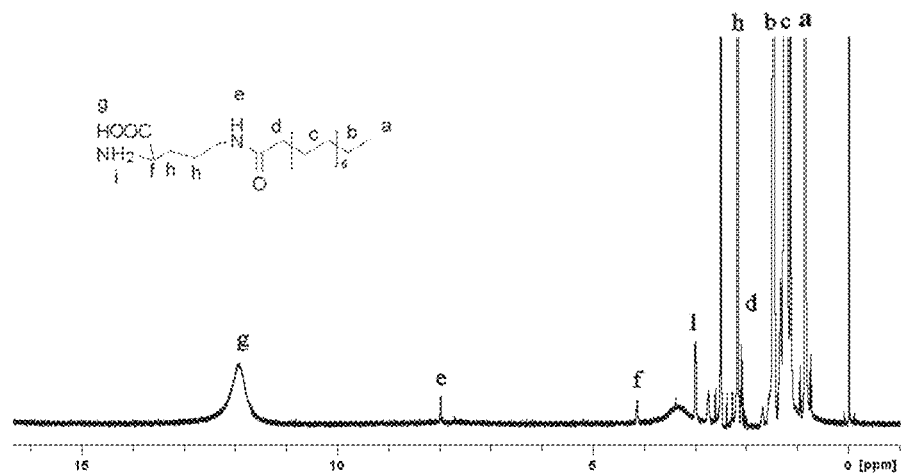
FIG. 2-1*a* shows the infrared spectrum of the platinum complex of Example 12.

The present invention provides a compound and use thereof, and a platinum complex and liposome thereof, which can be achieved by those skilled in the art in light of the disclosure by properly improving the process parameters. In particular, it should be noted that all similar substitutions and modifications will be apparent to those skilled in the art, and are all deemed to be included in the present invention. The method and application of the present invention have been described through preferred embodiments, The method and application of the present invention have been described by preferred examples thereof, and it is apparent that related individuals can make modifications or proper changes and combination to the methods and application described herein so as to achieve and apply the technology of the present application, without departing from the content, spirit and scope of the present invention.

The present invention provides a platinum complex having a structure represented by formulas I-a to I-d:

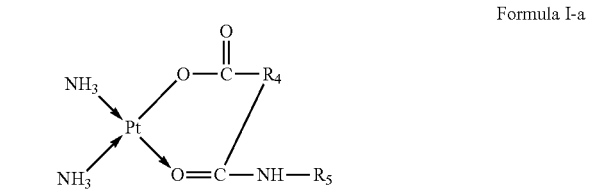

Formula I-a

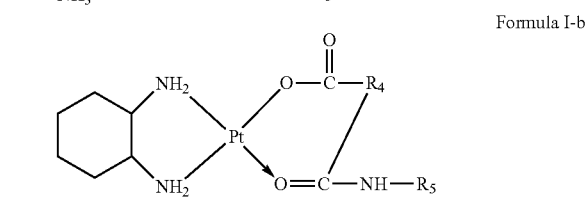

Formula I-b

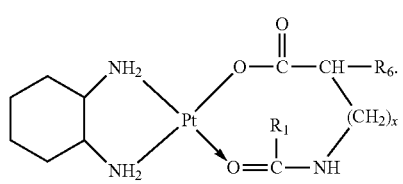

Formula I-c

Formula I-d $R_1$ is selected from the group consisting of —H, —$C_nH_{2n+1}$, —$C_nH_{2n-1}$, —Ar—$C_nH_{2n+1}$, —Ar—$C_nH_{2n-1}$, —Ar—O—$C_nH_{2n+1}$, and —Ar—O—$C_nH_{2n-1}$, with n=1~22;

$R_4$ is selected from the group consisting of —$C_bH_{2b}$—, —$C_bH_{2b-2}$—, —Ar—$C_bH_{2b}$—, —Ar—$C_bH_{2b-2}$—, —Ar—O—$C_bH_{2b}$—, —Ar—O—$C_bH_{2b-2}$—, and hyaluronic acid with two carboxyl groups removed, with b=0~22;

$R_5$ is selected from the group consisting of —H, —$C_cH_{2c+1}$, —$C_cH_{2c-1}$, —Ar—$C_cH_{2c+1}$, —Ar—$C_cH_{2c-1}$, —Ar—O—$C_cH_{2c+1}$, —Ar—O—$C_cH_{2c-1}$, and chitosan with one amino removed, with c=0~21;

$R_6$ is selected from the group consisting of —$NH_2$, —$C_dH_{2d}$—$NH_2$, —$C_dH_{2d-2}$—$NH_2$, —$C_dH_{2d}$—COOH, —$C_dH_{2d-2}$—COOH, —NH—CO—$(CH_2)_eCH_3$, and —$(CH_2)_d$NH—CO—$(CH_2)_eCH_3$, with d=1~8 and e=1~21; and x=0~10;

wherein H attached to any C can be substituted with a substituent;

wherein the substituent is one or more of —$NH_2$, —OH, —COOH, halogen and —Ar.

In the present invention, —$C_nH_{2n+1}$ or —$C_cH_{2c+1}$ is an alkyl group, wherein n is 1~22. In some embodiments, n is 8~20. In other embodiments, n is 8~18 or n is 12~18; in other embodiments, n is 14~16; and in some embodiments, n is 15. c may be the same as or different from n. Independently, c is 1~22. In some embodiments, c is 8~20. In other embodiments, c is 8~18 or c is 12~18; in other embodiments, c is 14~16; and in some embodiments, c is 15. The alkyl group is a linear or branched alkyl group; and in some embodiments, a linear alkyl group. The alkyl group is a substituted or unsubstituted alkyl group. The substitution means that H attached to any C in an alkyl group may be substituted with a substituent and the substituent for the substituted alkyl group is one or more of —$NH_2$, —OH, —COOH, halogen and —Ar. The number of substituent on any C is 1 or 2. In the present invention, the —$C_nH_{2n+1}$ alkyl group includes but not limited to, methyl (Me, —$CH_3$), ethyl (Et, —$CH_2CH_3$), n-propyl (n-Pr, —$CH_2CH_2CH_3$), isopropyl (i-Pr, —$CH(CH_3)_2$), n-butyl (n-Bu, —$CH_2CH_2CH_2CH_3$), isobutyl (i-Bu, —$CH_2CH(CH_3)_2$), sec-butyl (s-Bu, —$CH(CH_3)CH_2CH_3$), tert-butyl (t-Bu, —$C(CH_3)_3$), n-pentyl (—$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), n-hexyl (—$CH_2CH_2CH_2CH_2CH_2CH_3$), 2-hexyl (—CH($CH_3$)$CH_2CH_2CH_2CH_3$), 3-hexyl (—CH($CH_2CH_3$)($CH_2CH_2CH_3$)), 2-methyl-2-pentyl (C($CH_3$)$_2$$CH_2CH_2CH_3$), 3-methyl-2 pentyl (—CH($CH_3$)CH($CH_3$)$CH_2CH_3$), 4-methyl-2-pentyl (—CH($CH_3$)$CH_2CH(CH_3)_2$), 3-methyl-3-pentyl (—C($CH_3$)($CH_2CH_3$)$_2$), 2-methyl-3-pentyl (—CH($CH_2CH_3$)CH($CH_3$)$_2$), 2,3-dimethyl-2-butyl (—C($CH_3$)$_2$CH($CH_3$)$_2$), 3,3-dimethyl-2-butyl (—CH($CH_3$)C($CH_3$)$_3$), n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl.

In the present invention, —$C_nH_{2n-1}$ or —$C_cH_{2c-1}$ refers to an alkenyl group, wherein at least one position is unsaturated, i.e., a C—C is $sp^2$ double bond. n is 2~22. In some embodiments, n is 8~20. In other embodiments, n is 8~18 or n is 12~18; in other embodiments, n is 14~16; and in some embodiments, n is 15. C may be the same as or different from n, and independently, c is 2~22. In some embodiments, c is 8~20. In other embodiments, c is 8~18 or c is 12~18; in other embodiments, c is 14~16; and in some embodiments, c is 15. The alkenyl group is a linear or branched alkenyl group. In some embodiments, it is a linear alkenyl group. The alkenyl group is a substituted or unsubstituted alkenyl group. H attached to any C in the substituted alkenyl group may be substituted with a substituent, wherein the substituent in the substituted alkenyl group is one or more of —$NH_2$, —OH, —COOH, halogen and —Ar. The number of substituent on any C is 1 or 2. The alkenyl group includes a group with a "trans" "cis" or "E" "Z" orientation, and specific examples thereof include but are not limited to, vinyl (—CH=$CH_2$), propenyl, allyl (—$CH_2$CH=$CH_2$), butenyl and 4-methylbutenyl, 2-pentenyl, hexenyl, heptenyl, octenyl, nonenyl, decenyl, undecylenyl, dodecenyl, tridecenyl, tetradecenyl, pentadecenyl, hexadecenyl, heptadecenyl, and octadecenyl.

In the present invention, —Ar—$C_nH_{2n+1}$ refers to —$C_nH_{2n+1}$ linked to a phenyl or aryl group, —Ar—$C_nH_{2n-1}$ refers to —$C_nH_{2n-1}$ attached to a phenyl or aryl group, —Ar—O—$C_nH_{2n+1}$ refers to —$C_nH_{2n+1}$ linked to —Ar—O—, and —Ar—O—$C_nH_{2n-1}$ refers to —$C_nH_{2n-1}$ linked to —Ar—O—. —Ar—$C_cH_{2c+1}$ refers to —$C_cH_{2c+1}$ linked to a phenyl or aryl group, —Ar—$C_cH_{2c-1}$ refers to —$C_cH_{2c-1}$ attached to a phenyl or aryl group, —Ar—O—$C_cH_{2c+1}$ refers to —$C_cH_{2c+1}$ linked to —Ar—O—, and —Ar—O—$C_cH_{2c-1}$ refers to —$C_cH_{2c-1}$ linked to —Ar—O—. —Ar— represents a monocyclic, bicyclic, and tricyclic carbocyclic ring system containing a 6-14 membered ring in total, wherein at least one ring system is aromatic, wherein each ring system contains a 3-7 membered ring, and wherein there are two connection points connected to the rest of the molecule. —Ar— may be phenylene, naphthyl and anthrylene, and may be substituted or unsubstituted.

In the present invention, —$C_bH_{2b}$— or —$C_dH_{2d}$— refers to an alkylene group, and b is 1~8. In some embodiments, b is 1~6. In other embodiments, b is 1~4; and in other embodiments, b is 2~4. The alkylene group is a linear or branched alkylene group. d may be the same as or different from b, and independently, d is 1~8. In some embodiments, d is 1~6. In other embodiments, d is 1~4; and in other embodiments, d is 2~4. The alkylene group is a linear or branched alkylene group. In some embodiments, it is a linear alkylene group. The alkylene group is a substituted or unsubstituted alkylene group. The substitution means that H attached to any C in an alkylene group may be substituted with a substituent, wherein the substituent in the substituted alkyl group is one or more of —$NH_2$, —OH, —COOH, and —Ar. The number of substituents on any C is 1 or 2. In the present invention, the alkylene group includes but not limited to, methylene (—CH$_2$—), ethylene (—CH$_2$CH$_2$—), n-propylidene (—CH$_2$CH$_2$CH$_2$—), iso-propylidene (—C(CH$_3$)$_2$—), n-butylene (—CH$_2$CH$_2$CH$_2$CH$_2$—), isobutylene, sec-butylene, tert-butylene, n-pentylidene, 2-pentylidene, 3-pentylidene, 2-methyl-2-butylene, 3-methyl-2-butylene, 3-methyl-1-butylene, 2-methyl-1-butylene, n-hexylidene, 2-hexylidene, 3-hexylidene, 2-methyl-2-pentylidene, 3-methyl-2-pentylidene, 4-methyl-2-pentylidene, 3-methyl-3-pentylidene, 2-methyl-3-pentylidene, 2,3-dimethyl-2-butylene, 3,3-dimethyl-2-butylene, n-heptylidene, n-octylene, carboxy group-substituted propylidene, carboxy group-substituted n-butylene, carboxy group-substituted n-pentylidene, amino group-substituted propylidene, amino group-substituted n-butylene, amino group-substituted n-pentylidene.

In the present invention, —C$_b$H$_{2b-2}$— or —C$_d$H$_{2d-2}$— refers to an alkenylene group, wherein at least one position is unsaturated, i.e., a C—C is sp$^2$ double bond. B is 2~8. In some embodiments, b is 2~6. In other embodiments, b is 2~4. d may be the same as or different from b, and independently, d is 2~8. In some embodiments, d is 2~6. In other embodiments, d is 2~4. The alkenylene group is a linear or branched alkenylene group. In some embodiments, it is a linear alkenylene group. The alkenylene group is a substituted or unsubstituted alkenylene group. H attached to any C in the substituted alkenylene group may be substituted with a substituent, wherein the substituent in the substituted alkenylene group is one or more of —NH$_2$, —OH, —COOH, and —Ar. The number of substituents on any C is 1 or 2. The alkenylene group includes a group with a "trans" "cis" or "E" "Z" orientation, and specific examples thereof include but are not limited to, vinylene (—CH=CH—), propenylene, allylene (—CH$_2$CH=CH—), butenylene and 4-methylbutenylene, 2-pentenylene, hexenylene, heptenylene, octenylene.

In some embodiments of the present invention, —C$_d$H$_{2d}$—NH$_2$ or —C$_d$H$_{2d-2}$—NH$_2$ is —C$_d$H$_{2d}$— or —C$_d$H$_{2d-2}$— linked with an amino group (—NH$_2$); and —C$_d$H$_{2d}$—COOH or —C$_d$H$_{2d-2}$—COOH is —C$_d$H$_{2d}$— or —C$_d$H$_{2d-2}$—linked with a carboxyl group (—COOH).

In some embodiments,

R$_1$ is selected from the group consisting of —H, —C$_n$H$_{2n+1}$, and —C$_n$H$_{2n-1}$, with n=8~18;

R$_4$ is selected from the group consisting of —C$_b$H$_{2b}$—, —C$_b$H$_{2b-2}$—, and hyaluronic acid with two carboxyl groups removed, with b=1~10;

R$_5$ is selected from the group consisting of —C$_c$H$_{2c+1}$, —C$_c$H$_{2c-1}$, and chitosan with one amino group removed, with c=8~18; and R$_6$ is selected from the group consisting of —NH$_2$, —NH—CO—(CH$_2$)$_e$CH$_3$, —C$_d$H$_{2d}$—NH$_2$, —C$_d$H$_{2d}$—COOH, and —(CH$_2$)$_d$NH—CO—(CH$_2$)$_e$CH$_3$, with d=2~6 and e=8~18.

In some embodiments, x=0~6;

R$_1$ is —C$_n$H$_{2n+1}$, with n=8~18;

R$_4$ is selected from the group consisting of —CH$_2$—,

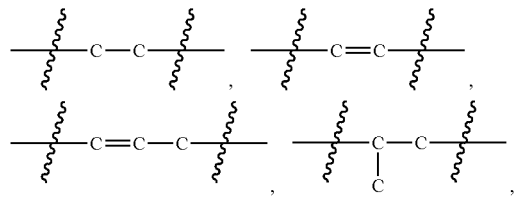

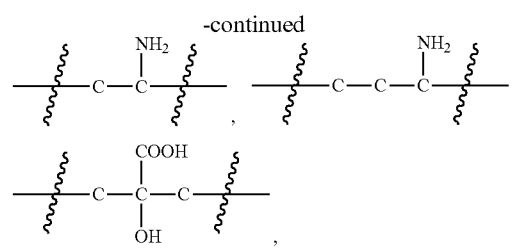

and hyaluronic acid with two carboxyl groups removed;

R$_5$ is selected from the group consisting of —C$_c$H$_{2c+1}$, with c=12~18; and R$_6$ is selected from the group consisting of —NH$_2$, —(CH$_2$)$_4$NH$_2$, —(CH)$_2$—COOH, and —(CH$_2$)$_4$NH—CO—(CH$_2$)$_{14}$CH$_3$.

In some embodiments, x=0; R$_1$ is —C$_n$H$_{2n+1}$, with n=8~18; and R$_6$ is —CH$_2$—COOH, —(CH$_2$)$_4$NH$_2$, —(CH$_2$)$_2$—COOH, or —(CH$_2$)$_4$NH—CO—(CH$_2$)$_{14}$CH$_3$.

In some embodiments, x=1~6; R$_1$ is —C$_n$H$_{2n+1}$, with n=8~18; and R$_6$ is —NH$_2$.

The platinum complexes provided by the present invention are presented by formulas (1)-(22), with y=7~17:

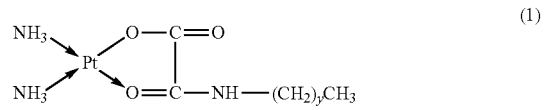

(1)

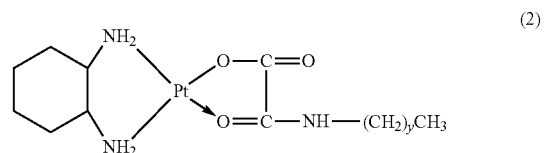

(2)

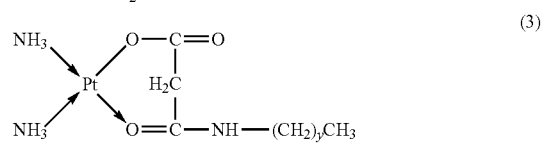

(3)

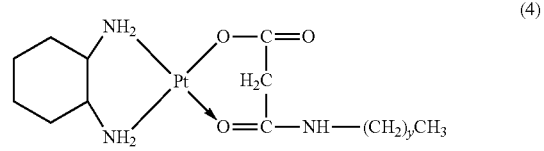

(4)

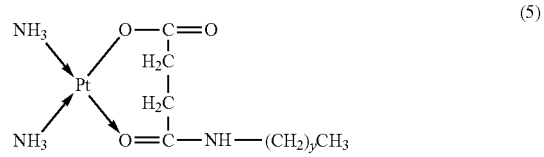

(5)

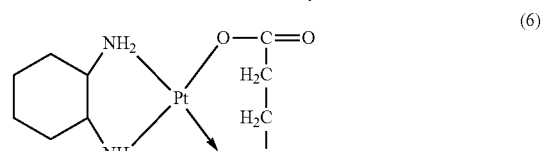

(6)

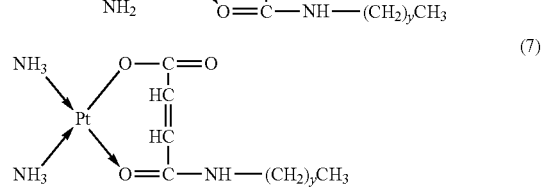

(7)

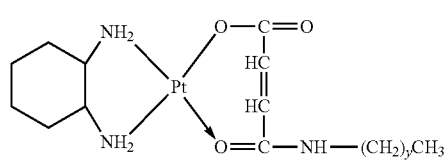
(8)
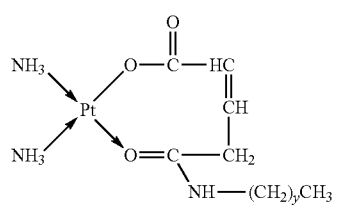
(9)
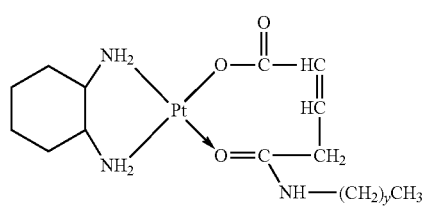
(10)
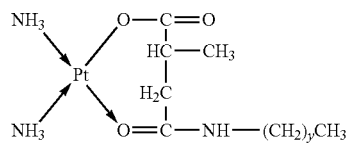
(11)
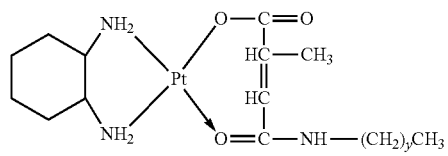
(12)
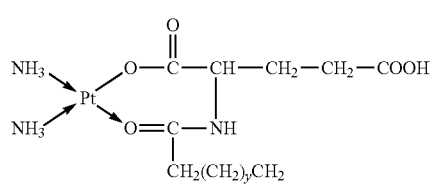
(13)
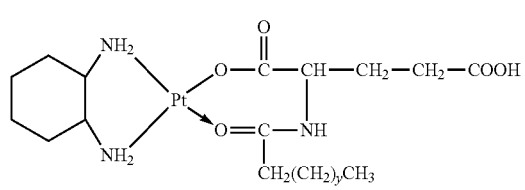
(14)
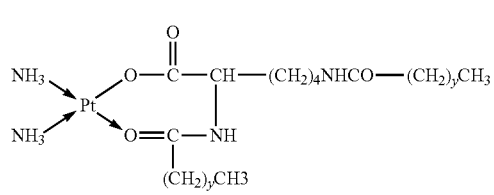
(15)
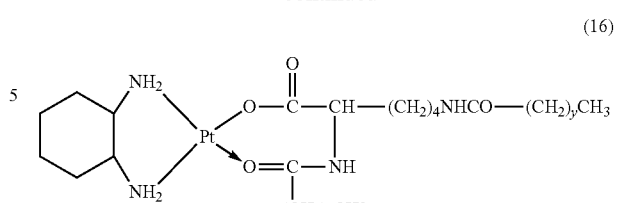
(16)
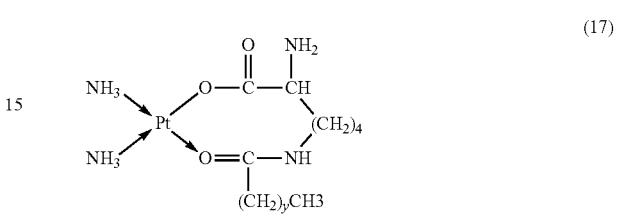
(17)
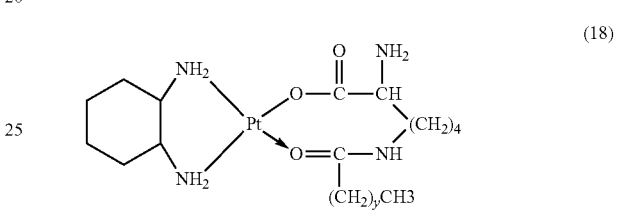
(18)
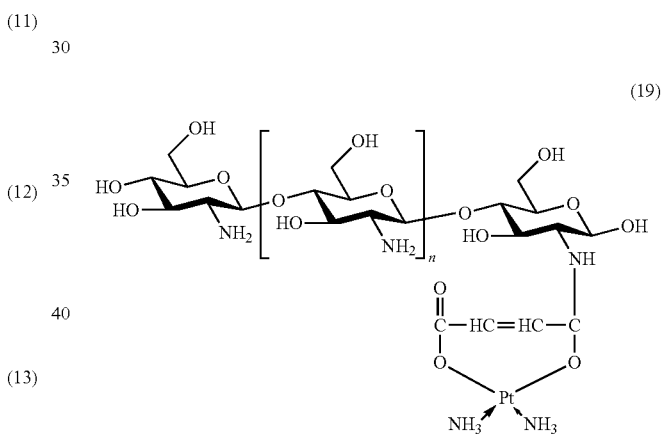
(19)
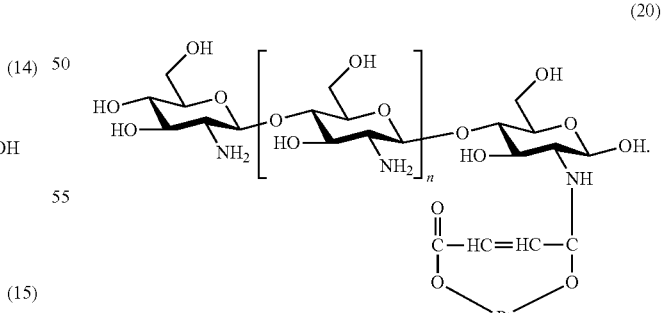
(20)

(21)

(22)

In the structural formulas (1)-(22) of the platinum complexes provided by the present invention, y=7, 8, 9, 10, 11, 12, 13, 14, 15, 16, or 17.

The platinum complex provided by the present invention is prepared by reacting a compound of Formula II or III with a platinum compound, wherein the platinum compound is cisplatin, carboplatin, oxaliplatin or nedaplatin, eptaplatin, lobaplatin, and the like.

Formula II $$R_1-C(=O)-NH-R_2-C(=O)-R_3$$

Formula III $$HO-C(=O)-R_4-C(=O)-NH-R_5$$

$R_1$ is selected from the group consisting of —H, —$C_nH_{2n+1}$, —$C_nH_{2n-1}$, —Ar—$C_nH_{2n+1}$, —Ar—$C_nH_{2n-1}$, —Ar—O—$C_nH_{2n+1}$, and —Ar—O—$C_nH_{2n-1}$, with n=1~22;

$R_2$ is selected from the group consisting of —$C_mH_{2m}$—, —$C_mH_{2m-2}$—, —$C_mH_{2m}$—NH—, and —$C_mH_{2m-2}$—NH—, with m=1~8;

$R_3$ is selected from the group consisting of —OH, —$C_aH_{2a+1}$, —$C_aH_{2a-1}$, —Ar—$C_aH_{2a+1}$, —Ar—$C_aH_{2a-1}$, —Ar—O—$C_aH_{2a+1}$, and —Ar—O—$C_aH_{2a-1}$, with a=1~22;

$R_4$ is selected from the group consisting of —$C_bH_{2b}$—, —$C_bH_{2b-2}$—, —Ar—$C_bH_{2b}$—, —Ar—$C_bH_{2b-2}$—, —Ar—O—$C_bH_{2b}$—, —Ar—O—$C_bH_{2b-2}$—, and hyaluronic acid with two carboxyl groups removed, with b=0~22;

$R_5$ is selected from the group consisting of —H, —$C_cH_{2c+1}$, —$C_cH_{2c-1}$, —Ar—$C_cH_{2c+1}$, —Ar—$C_cH_{2c-1}$, —Ar—O—$C_cH_{2c+1}$, —Ar—O—$C_cH_{2c-1}$, and chitosan with one amino group removed, with c=0~22;

wherein H attached to any C can be substituted with a substituent;

wherein the substituent is one or more of —$NH_2$, —OH, —COOH, halogen and —Ar; and $R_2$ and $R_3$ comprise in structure at least one —COOH.

In the method provided by the present invention, the molar ratio of the compound of Formula II or III to Pt in the platinum compound is not more than 30:1.

In some embodiments, the molar ratio of the compound of Formula II or III to Pt in the platinum compound is (1~8):1.

In other embodiments, the molar ratio of the compound of Formula II or III to Pt in the platinum compound is (1~5):1.

In other embodiments, the molar ratio of the compound of Formula II or III to Pt in the platinum compound is 1:1.

The solvent used in the preparation of the platinum complex is an aqueous medium.

In embodiments provided by the present invention, the aqueous medium either is water or mannitol aqueous solution or sodium chloride aqueous solution or glycerin aqueous solution or sugar-containing aqueous solution or phosphate buffer, and the like (but not limited to thereto), or may be the above aqueous solution containing dimethylformamide (DMF), dimethylsulfoxide (DMSO).

The present invention provides an amphiphilic compound having a structure represented by Formula II:

Formula II $$R_1-C(=O)-NH-R_2-C(=O)-R_3,$$

wherein:

$R_1$ is selected from the group consisting of —H, —$C_nH_{2n+1}$, —$C_nH_{2n-1}$, —Ar—$C_nH_{2n+1}$, —Ar—$C_nH_{2n-1}$, —Ar—O—$C_nH_{2n+1}$, and —Ar—O—$C_nH_{2n-1}$, with n=1~22;

$R_2$ is selected from the group consisting of —$C_mH_{2m}$—, —$C_mH_{2m-2}$—, —$C_mH_{2m}$—NH—, and —$C_mH_{2m-2}$—NH—, with m=1~8; and $R_3$ is selected from the group consisting of —OH, —$C_aH_{2a+1}$, —Ar—$C_aH_{2a+1}$, —Ar—$C_aH_{2a-1}$, —Ar—O—$C_aH_{2a+1}$, and —Ar—O—$C_aH_{2a-1}$, with a=1~22;

wherein H attached to any C can be substituted with a substituent;

wherein the substituent is one or more of —$NH_2$, —OH, —COOH, halogen, and —Ar;

$R_2$ and $R_3$ comprise in structure at least one —COOH.

In the present invention, —$C_nH_{2n+1}$ or —$C_aH_{2a+1}$ is an alkyl group, wherein n is 1~22. In some embodiments, n is 8~20. In other embodiments, n is 8~18 or n is 12~18; in other embodiments, n is 14~16; and in some embodiments, n is 15. a may be the same as or different from n. Independently, a is 1~22. In some embodiments, a is 8~20. In other embodiments, a is 8~18 or a is 12~18; in other embodiments, a is 14~16; and in some embodiments, a is 15. The alkyl group is a linear or branched alkyl group; and in some embodiments, a linear alkyl group. The alkyl group is a substituted or unsubstituted alkyl group. The substitution means that H attached to any C in an alkyl group may be substituted with a substituent and the substituent for the substituted alkyl group is one or more of —$NH_2$, —OH, —COOH, and —Ar. The number of substituents on any C is 1 or 2. In the present invention, the —$C_nH_{2n+1}$ alkyl group includes but not limited to, methyl (Me, —$CH_3$), ethyl (Et, —$CH_2CH_3$), n-propyl (n-Pr, —$CH_2CH_2CH_3$), isopropyl (i-Pr, —$CH(CH_3)_2$), n-butyl (n-Bu, —$CH_2CH_2CH_2CH_3$), isobutyl (i-Bu, —$CH_2CH(CH_3)_2$), sec-butyl (s-Bu, —CH($CH_3$)$CH_2CH_3$), tert-butyl (t-Bu, —C($CH_3$)$_3$), n-pentyl (—$CH_2CH_2CH_2CH_2CH_3$), 2-pentyl (—CH($CH_3$)$CH_2CH_2CH_3$), 3-pentyl (—CH($CH_2CH_3$)$_2$), 2-methyl-2-butyl (—C($CH_3$)$_2CH_2CH_3$), 3-methyl-2-butyl (—CH($CH_3$)CH($CH_3$)$_2$), 3-methyl-1-butyl (—$CH_2CH_2CH(CH_3)_2$), 2-methyl-1-butyl (—$CH_2CH(CH_3)CH_2CH_3$), n-hexyl (—$CH_2CH_2CH_2CH_2CH_2CH_3$), 2-hexyl (—CH($CH_3$)$CH_2CH_2CH_2CH_3$), 3-hexyl (—CH($CH_2CH_3$)($CH_2CH_2CH_3$)), 2-methyl-2-pentyl (C($CH_3$)$_2CH_2CH_2CH_3$), 3-methyl-2 pentyl (—CH($CH_3$)CH($CH_3$)$CH_2CH_3$), 4-methyl-2-pentyl (—CH($CH_3$)$CH_2CH(CH_3)_2$), 3-methyl-3-pentyl (—C($CH_3$)($CH_2CH_3$)$_2$), 2-methyl-3-pentyl (—CH($CH_2CH_3$)CH($CH_3$)$_2$), 2,3-dimethyl-2-butyl (—C($CH_3$)$_2CH(CH_3)_2$), 3,3-dimethyl-2-butyl (—CH($CH_3$)C($CH_3$)$_3$), n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl.

In the present invention, —$C_nH_{2n-1}$ or —$C_aH_{2a-1}$ refers to an alkenyl group, wherein at least one position is unsaturated, i.e., a C—C is sp$^2$ double bond. N is 2~22. In some embodiments, n is 8~20. In other embodiments, n is 8~18 or n is 12~18; in other embodiments, n is 14~16; and in some embodiments, n is 15. a may be the same as or different from n, and independently, a is 2~22. In some embodiments, a is 8~20. In other embodiments, a is 8~18 or a is 12~18; in other embodiments, a is 14~16; and in some embodiments, a is 15. The alkenyl group is a linear or branched alkenyl group. In some embodiments, it is a linear alkenyl group. The alkenyl group is a substituted or unsubstituted alkenyl group. H attached to any C in the substituted alkenyl group may be substituted with a substituent, wherein the substituent in the substituted alkenyl group is one or more of —$NH_2$, —OH, —COOH, halogen and —Ar. The number of substituents on any C is 1 or 2. The alkenyl group includes a group with a "trans" "cis" or "E" "Z" orientation, and specific examples thereof include but are not limited to, vinyl (—CH=$CH_2$), propenyl, allyl (—$CH_2CH$=$CH_2$), butenyl and 4-methylbutenyl, 2-pentenyl, hexenyl, heptenyl, octenyl, nonenyl, decenyl, undecylenyl, dodecenyl, tridecenyl, tetradecenyl, pentadecenyl, hexadecenyl, heptadecenyl, octadecenyl.

In the present invention, —Ar—$C_nH_{2n+1}$ refers to —$C_nH_{2n+1}$ linked to a phenyl or aryl group, —Ar—$C_nH_{2n-1}$ refers to —$C_nH_{2n-1}$ attached to a phenyl or aryl group, —Ar—O—$C_nH_{2n+1}$ refers to —$C_nH_{2n+1}$ linked to —Ar—O—, and —Ar—O—$C_nH_{2n-1}$ refers to —$C_nH_{2n-1}$ linked to —Ar—O—. —Ar—$C_aH_{2a+1}$ refers to —$C_aH_{2a+1}$ linked to a phenyl or aryl group, —Ar—$C_aH_{2a-1}$ refers to —$C_aH_{2a-1}$ attached to a phenyl or aryl group, —Ar—O—$C_aH_{2a+1}$ refers to —$C_aH_{2a+1}$ linked to —Ar—O—, and —Ar—O—$C_aH_{2a-1}$ refers to —$C_aH_{2a-1}$ linked to —Ar—O—. —Ar— represents a monocyclic, bicyclic, and tricyclic carbocyclic ring system containing a 6~14 membered ring in total, wherein at least one ring system is aromatic, wherein each ring system contains a 3-7 membered ring, and wherein there are two connection points connected to the rest of the molecule. —Ar— may be phenylene, naphthyl or anthrylene, and may be substituted or unsubstituted.

In the present invention, —$C_mH_{2m}$— refers to an alkylene group, and m is 1~8. In some embodiments, m is 1~6. In other embodiments, m is 1~4; and in other embodiments, m is 2~4. The alkylene group is a linear or branched alkylene group. In some embodiments, it is a linear alkylene group.

The alkylene group is a substituted or unsubstituted alkylene group. The substitution means that H attached to any C in an alkylene group may be substituted with a substituent, wherein the substituent in the substituted alkyl group is one or more of —$NH_2$, —OH, —COOH, and —Ar. The number of substituent on any C is 1 or 2. In the present invention, the —$C_mH_{2m}$— alkylene group includes but not limited to, methylene (—$CH_2$—), ethylene (—$CH_2CH_2$—), n-propylidene (—$CH_2CH_2CH_2$—), iso-propylidene (—C($CH_3$)$_2$—), n-butylene (—$CH_2CH_2CH_2CH_2$—), isobutylene, sec-butylene, tert-butylene, n-pentylidene, 2-pentylidene, 3-pentylidene, 2-methyl-2-butylene, 3-methyl-2-butylene, 3-methyl-1-butylene, 2-methyl-1-butylene, n-hexylidene, 2-hexylidene, 3-hexylidene, 2-methyl-2-pentylidene, 3-methyl-2-pentylidene, 4-methyl-2-pentylidene, 3-methyl-3-pentylidene, 2-methyl-3-pentylidene, 2,3-dimethyl-2-butylene, 3,3-dimethyl-2-butylene, n-heptylidene, n-octylene, carboxy group-substituted propylidene, carboxy group-substituted n-butylene, carboxy group-substituted n-pentylidene, amino group-substituted propylidene, amino group-substituted n-butylene, amino group-substituted n-pentylidene.

In the present invention, —$C_mH_{2m-2}$— refers to an alkenylene group, wherein at least one position is unsaturated, i.e., a C—C is sp$^2$ double bond. n is 2~8. In some embodiments, n is 2~6. In other embodiments, n is 2~4. The alkenylene group is a linear or branched alkenylene group. In some embodiments, it is a linear alkenylene group. The alkenylene group is a substituted or unsubstituted alkenylene group. H attached to any C in the substituted alkenylene group may be substituted with a substituent, wherein the substituent in the substituted alkenylene group is one or more of —$NH_2$, —OH, —COOH, and —Ar. The number of substituent on any C is 1 or 2. The alkenylene group includes a group with a "trans" "cis" or "E" "Z" orientation, and specific examples thereof include but are not limited to, vinylene (—CH=CH—), propenylene, allylene (—$CH_2CH$=CH—), butenylene and 4-methylbutenylene, 2-pentenylene, hexenylene, heptenylene, octenylene.

In the present invention, —$C_mH_{2m}$—NH— or —$C_mH_{2m-2}$—NH— refers to —$C_mH_{2m}$— or —$C_mH_{2m-2}$— linked with —NH—.

In some embodiments of the present invention, in the amphipathic compound:

$R_1$ is selected from the group consisting of —$C_nH_{2n+1}$ and —$C_nH_{2n-1}$, with n=8~18;

$R_2$ is selected from the group consisting of —$C_mH_{2m}$— and —$C_mH_{2m-1}$—NH—, with m=2~6; and $R_3$ is selected from the group consisting of —OH, —$C_aH_{2a+1}$, and —$C_aH_{2a-1}$, with a=8~18;

wherein H attached to any C can be substituted with one or two substituents; and wherein the substituent is —$NH_2$ or —COOH.

$R_2$ and $R_3$ comprise in structure at least one —COOH.

In some embodiments of the present invention, $R_1$ is —$C_nH_{2n+1}$, $R_2$ is

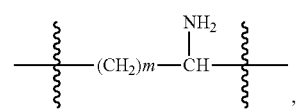

and $R_3$ is —OH;

or $R_1$ is $—C_nH_{2n+1}$, $R_2$ is

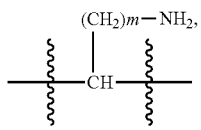

and $R_3$ is —OH;
or $R_1$ is $—C_nH_{2n+1}$, $R_2$ is

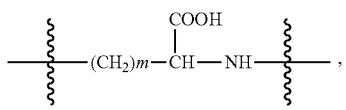

and $R_3$ is $—C_aH_{2a+1}$;
or $R_1$ is $—C_nH_{2n+1}$, $R_2$ is

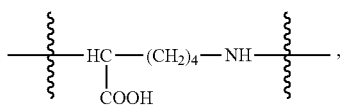

and $R_3$ is $—C_aH_{2a+1}$.

In some embodiments of the present invention, the amphiphilic compound has a structure of:

Formula II-a

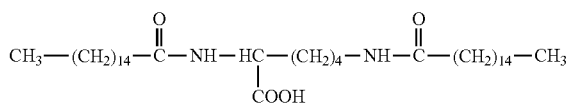

Formula II-b

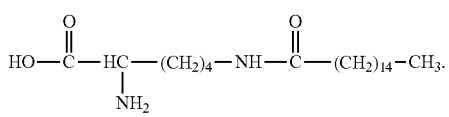

The platinum complex provided by the present invention can bind to the membrane material of the liposome well, thereby improving the encapsulation ratio and drug loading of the liposome. In addition, the platinum complex prepared from the compound provided by the present invention has a carboxyl group which is pH-sensitive, thus in the environment with a low pH (such as tumor tissue), the carboxyl group tends to be deprotonated, which is favorable for promoting the release of the drug in the tumor tissue, thereby improving the therapeutic effect thereof and reducing the toxic side effects thereof.

The present invention further provides a platinum complex liposome, comprising the platinum complex provided by the present invention, a lipid membrane material and/or a stabilizer, wherein the ratio of the platinum complex to the lipid membrane material is (99:1) to (1:99).

The ratio is on a mass, molar or volume basis.

In the liposome provided by the present invention, the lipid membrane material comprises a composition of phospholipid and/or cholesterol, wherein the lipid membrane material comprises 1-100 parts phospholipid and 0-60 parts cholesterol by mass.

In some embodiments of the present invention, the phospholipid is any one or a composition of two or more of egg-yolk lecithin, soy lecithin, hydrogenated soya phospholipid, phosphatidylserine, phosphatidylinositol, phosphatidylethanolamine, phosphatidylglycerol, dilauroylphosphatidylcholine, dimyristoylphosphatidylcholine, dipalmitoylphosphatidylcholine, distearoylphosphatidylcholine dioleoylphosphatidylcholine, dilauroylphosphatidylglycerol, dimyristoylphosphatidylglycerol, dipalmitoylphosphatidylglycerol, distearoylphosphatidylglycerol, dioleoylphosphatidylglycerol, phosphoglycerol, dierucoylphosphatidylglycerol, PEGylated phospholipid, and the like.

The liposome provided by the present invention alternatively further comprises a long-circulating material. The long-circulating material used in the present invention includes MPEG2000-DSPE, MPEG5000-DSPE, MPEG2000-DMPE, MPEG5000-DMPE, MPEG2000-DPPE, MPEG5000-DPPE, and the like.

The liposome provided by the present invention comprises the long-circulating material in a mass fraction of 0-50%.

The liposome provided by the present invention may further comprise an antioxidant. The antioxidant used in the present invention includes any one or a composition of two or more of L-cysteine, ascorbic acid, dl-α-tocopherol, sodium sulfite, sodium metabisulfite and anhydrous sodium bisulfate.

In the liposome provided by the present invention, the mass fraction of the antioxidant is not more than 20%.

In the liposome provided by the present invention, an isotonicity adjusting agent may further be added. The isotonicity adjusting agent includes any one or a composition of two or more of mannitol, sorbitol, glucose, sucrose, and sodium chloride.

The liposome provided by the present invention can be prepared by film dispersion, reverse evaporation, or double-emulsion method.

In some embodiments, the liposome is prepared by: taking a film material, an antioxidant, and a long-circulating material into a round bottom flask, adding an appropriate amount of an organic solvent to dissolve, adding the aqueous solution of the platinum complex provided by the present invention, and performing mechanical or ultrasonic homogenization to form a W/O emulsion, performing rotary evaporation under reduced pressure to remove the organic solvent to form a thin film on the wall of the container, then injecting a hydration medium, allowing the membrane material to be hydrated for 1 h-2 h, passing the resulting mixture through a liposome extruder or homogenizing to obtain a novel platinum-based liposome with a uniform particle size. The long-circulating material can also be added after liposome formation, stirred, and modified onto the liposome surface.

In other embodiments, the liposome is prepared by: taking a film material, an antioxidant, the platinum complex provided by the present invention, and a long-circulating material into a round bottom flask, adding an appropriate amount of an organic solvent to dissolve, performing rotary evaporation under reduced pressure to remove the organic solvent to form a thin film on the wall of the container, then injecting a hydration medium, allowing the membrane material to be hydrated for 1 h-2 h, passing the resulting mixture through a liposome extruder or homogenizing to obtain a novel platinum-based liposome.

In other embodiments, the liposome is prepared by: taking a film material, an antioxidant, and a long-circulating material into a round bottom flask, adding an appropriate amount of an organic solvent to dissolve, adding the platinum complex provided by the present invention, and performing ultrasonic or mechanical homogenization to form a W/O emulsion, followed by rotary evaporation under reduced pressure to remove part of the organic solvent, then injecting a hydration medium to form W/O/W through mechanically stirring, performing rotary evaporation under reduced pressure to remove the organic solvent, passing the resulting mixture through a liposome extruder or homogenizing to obtain a novel platinum-based liposome.

The present invention further provides a medicament for the treatment of cancers, comprising the liposome and the preparation provided by the present invention.

The medicament provided by the present invention can be used to treat cancers such as breast cancer, non-small cell lung cancer, testicular cancer, pancreatic cancer, rectal cancer, liver cancer, ovarian cancer or head and neck cancer.

The dosage form of the medicament provided by the present invention includes injection (suspension type or lyophilized powder for injection), emulsion, submicroemulsion, and the like.

Experiments have shown that the liposome provided by the present invention can significantly increase the plasma concentration of the platinum compound, prolong the residence time of the drug in vivo, and can concentrate the platinum drug in the cancerous organ, which can not only reduce the dosage of the drug and increase the therapeutic effect thereof, but also can reduce the toxic side effects of the drug, thereby it is suitable for the treatment of various tumor diseases.

The present invention provides a compound having a structure represented by Formula II with a good biocompatibility, the carboxyl and amide groups of which are capable of complexing with a platinum-based drug to form unstable coordination bonds therewith, increasing the hydration rate of the drug in vivo and thereby improving the pharmaceutical effect thereof. At the same time, the platinum complex prepared from the compound provided by the present invention can bind to the membrane material of the liposome well, thereby improving the encapsulation ratio and drug loading of the liposome. In addition, the platinum complex prepared from the compound provided by the present invention has a carboxyl group which is pH-sensitive, wherein in the environment with a low pH value (such as tumor tissue), the carboxyl group tends to be deprotonated, which is favorable for promoting the release of the drug in the tumor tissue, thereby further improving the therapeutic effect thereof and reducing the toxic side effects thereof. Experiments demonstrate that the liposome provided by the present invention can significantly reduce the toxic side effects of a drug and improve the therapeutic effect thereof.

EXAMPLES

The reagents or instruments used in the present invention are all common products available on the market.

Hereinafter, the present invention will be further illustrated in combination with the examples:

Examples 1-8: Amphiphilic Compounds and Preparation Thereof

| | Starting materials for synthesis | | |
|---|---|---|---|
| Example No. | Acid | Aliphatic amine | Amphipathic compound |
| Example 1 | Maleic anhydride | Dodecylamine | $CH_3(CH_2)_{11}NH-\overset{O}{\overset{\|}{C}}-CH=CH-COOH$ |
| Example 2 | Maleic anhydride | Tetradecylamine | $CH_3(CH_2)_{13}NH-\overset{O}{\overset{\|}{C}}-CH=CH-COOH$ |
| Example 3 | Maleic anhydride | Hexadecylamine | $CH_3(CH_2)_{15}NH-\overset{O}{\overset{\|}{C}}-CH=CH-COOH$ |
| Example 4 | Maleic anhydride | Octadecylamine | $CH_3(CH_2)_{17}NH-\overset{O}{\overset{\|}{C}}-CH=CH-COOH$ |
| Example 5 | Butanedioic anhydride | Octadecylamine | $CH_3(CH_2)_{17}NH-\overset{O}{\overset{\|}{C}}-CH_2-CH_2-COOH$ |
| Example 6 | Acetic anhydride | Octadecylamine | $CH_3(CH_2)_{17}NH-\overset{O}{\overset{\|}{C}}-\overset{O}{\overset{\|}{C}}-OH$ |
| Example 7 | Propanoic anhydride | Octadecylamine | $CH_3(CH_2)_{17}NH-\overset{O}{\overset{\|}{C}}-CH_2-COOH$ |
| Example 8 | Methyl-butanedioic anhydride | Octadecylamine | $CH_3(CH_2)_{17}NH-\overset{O}{\overset{\|}{C}}-CH_2-\overset{CH_3}{\overset{\|}{CH}}-COOH$ |

Method for preparing amphiphilic compounds:

1. Examples 1-5

Figure 1A:
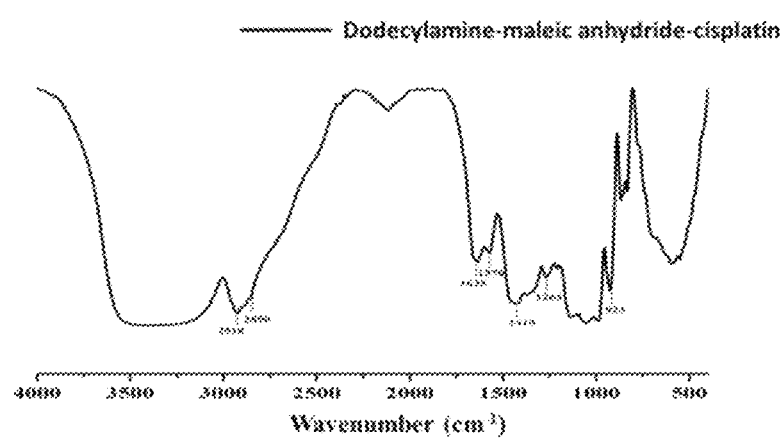

1.5 mmol of aliphatic amine (such as octadecylamine, hexadecylamine, tetradecylamine or dodecylamine, etc.) was measured and dissolved in 20 mL chloroform. Then, 3.3 mmol of anhydride (such as maleic anhydride or butanedioic anhydride) was measured and dissolved in 20 mL chloroform. Following the dissolution, the solution of aliphatic amine in chloroform was added to the anhydride solution, stirred for 30 min, and filtered under reduced pressure. The obtained product was washed with chloroform and acetone in sequence, and then dried (with a feeding molar ratio of 1:2) to obtain the above amphipathic compounds (Examples 1-5). The obtained amphiphilic compounds were characterized by nuclear magnetic resonance spectrum and the results were shown in FIGS. 1-a to 1-e.

2. Examples 6-8

1.5 mmol of octadecylamine was measured and dissolved in 20 mL dichloromethane. Then, 3.3 mmol of acid (such as acetic anhydride, propionic anhydride, methyl butanedioic anhydride) was measured and dissolved in 20 mL dichloromethane. The solution of aliphatic amine in dichloromethane was added to the anhydride solution, stirred for 30 min, and filtered under reduced pressure. The obtained product was washed with dichloromethane and acetone in sequence, and then dried (with a feeding molar ratio of 1:2) to obtain the above amphipathic compounds (Examples 6-8).

Example 9: Amphipathic Compound and Preparation Thereof

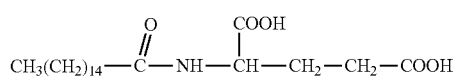

Method for preparing the amphipathic compound:

The amphipathic compound was synthesized by reacting palmitoyl chloride with glutamic acid under the specific reaction conditions as follows:

10 mmol of glutamic acid was suspended in 10 ml of DMF, placed in 45° C. oil bath and stirred. 12 mmol of palmitoyl chloride was added dropwise until glutamic acid was completely dissolved. 200 µl of triethylamine was added and stirred for 1-2 h. 100 ml distilled water was added and pH was adjusted to 1-2 with 1M HCl. Suction filtration was performed under reduced pressure and the obtained product was washed with water, followed by drying in an oven at 50° C. The product was taken out and washed three times with a mixed solvent of petroleum ether:acetone:ethyl acetate (100:1:1) with heating. The product was centrifuged, taken out and dried under reduced pressure.

Figures 1B, 2:
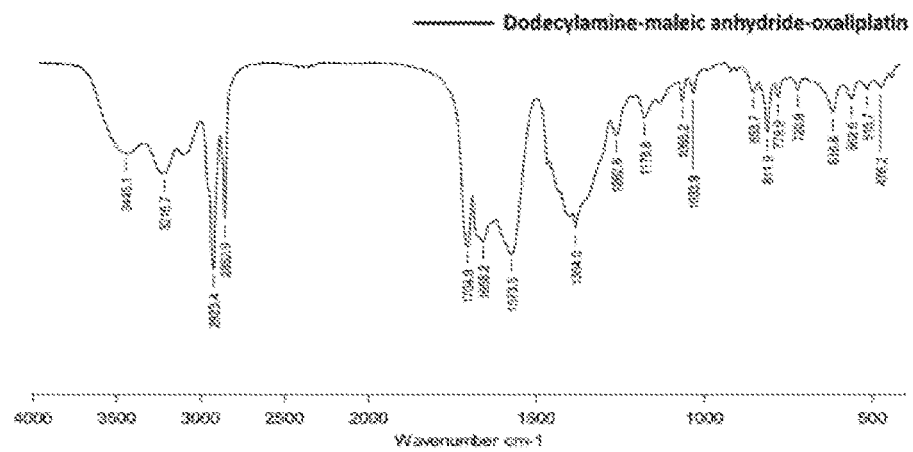
Figures 2, 2A:
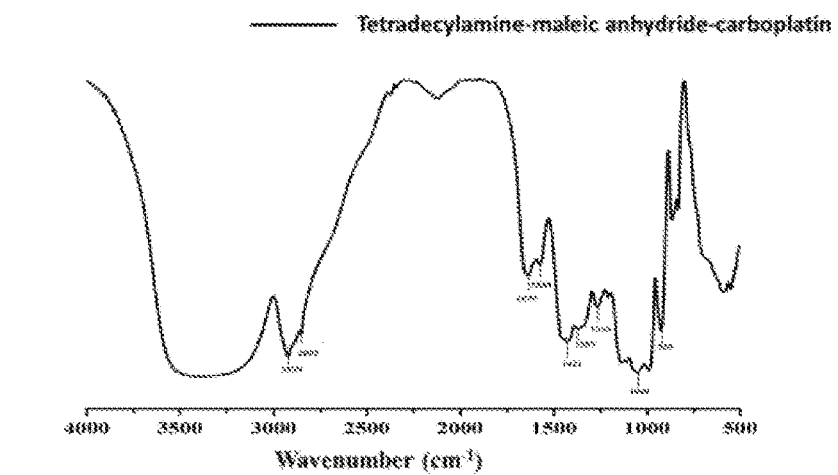
Figures 2, 2B:
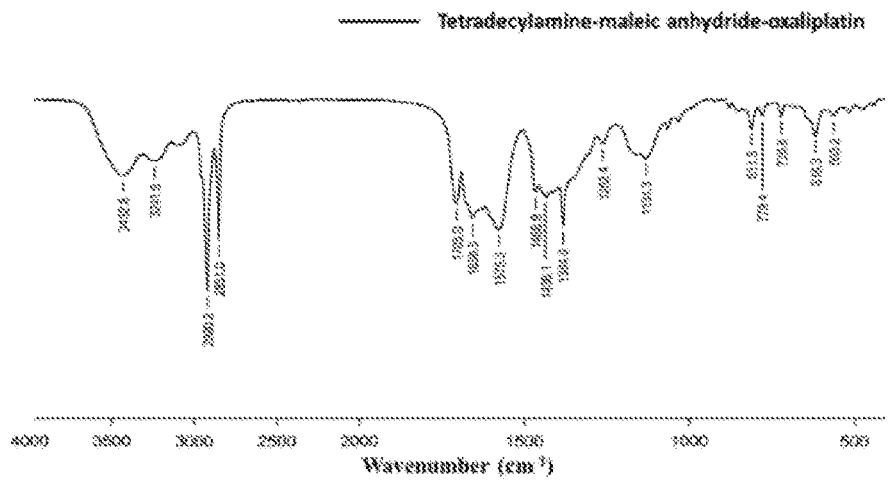

The obtained compound was characterized by nuclear magnetic resonance spectrum and the result was shown in FIG. 1-f.

Example 10: Amphipathic Compound and Preparation Thereof

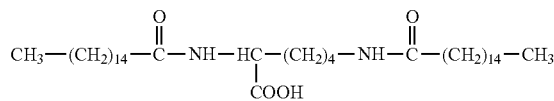

Method for preparing the amphipathic compound:

10 mmol of lysine was suspended in 10 ml of DMF, placed in 45° C. oil bath and stirred. 24 mmol of palmitoyl chloride was added dropwise until lysine was completely dissolved. 200 µl of triethylamine was added and stirred for 1-2 h. 100 ml distilled water was added and pH was adjusted to 1-2 with 1M HCl. Suction filtration was performed under reduced pressure and the obtained product was washed with water.

The washed product was dried in an oven at 50° C. The product was taken out and washed three times with a mixed solvent of petroleum ether:acetone:ethyl acetate (100:1:1) with heating. The product was centrifuged, taken out and dried under reduced pressure. The obtained compound was characterized by nuclear magnetic structure and the result was shown in FIG. 1-g.

Example 11: Amphiphilic Compound and Preparation Thereof

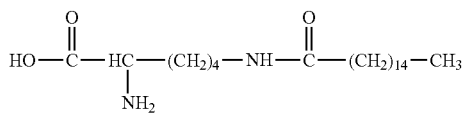

Method for preparing the amphipathic compound:

10 mmol of lysine was suspended in 10 ml of DMF, placed in 45° C. oil bath and stirred. 12 mmol of palmitoyl chloride was added dropwise until lysine was completely dissolved. 200 µl of triethylamine was added and stirred for 1-2 h. 100 ml distilled water was added and pH was adjusted to 1-2 with 1M HCl. Suction filtration was performed under reduced pressure and the obtained product was washed with water. The washed product was dried in an oven at 50° C. The product was taken out and washed three times with a mixed solvent of petroleum ether:acetone:ethyl acetate (100:1:1) with heating. The product was centrifuged, taken out and dried under reduced pressure.

The obtained compound was characterized by nuclear magnetic resonance spectrum and the result was shown in FIG. 1-h.

Examples 12-27: Preparation of Platinum Complexes

TABLE 1

Examples 12-27

| Example No. | Platinum compound | Amphiphilic compound | Prepared platinum complex |
|---|---|---|---|
| Example 12 | Cisplatin | Example 1 | 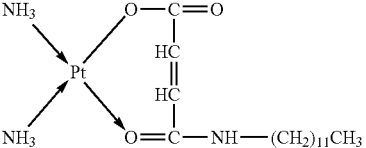 |
| Example 13 | Oxaliplatin | Example 1 | 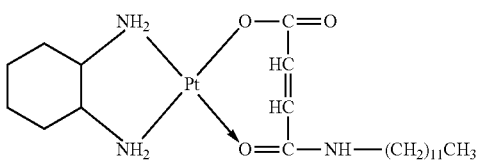 |
| Example 14 | Carboplatin | Example 2 | 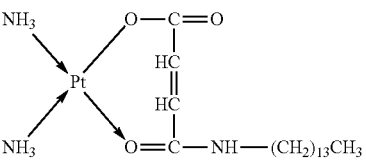 |
| Example 15 | Oxaliplatin | Example 2 | 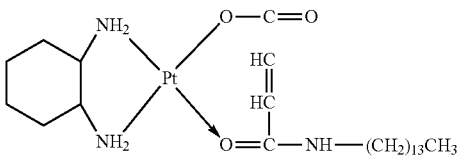 |
| Example 16 | Cisplatin | Example 3 | 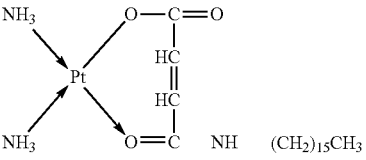 |
| Example 17 | Oxaliplatin | Example 3 | 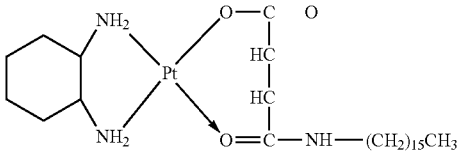 |
| Example 18 | Cisplatin | Example 4 | 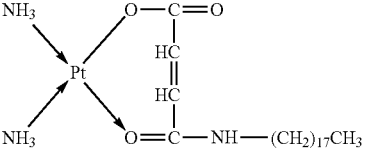 |
| Example 19 | Oxaliplatin | Example 4 | 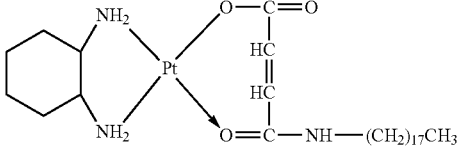 |

TABLE 1-continued
Examples 12-27
| Example No. | Platinum compound | Amphiphilic compound | Prepared platinum complex |
|---|---|---|---|
| Example 20 | Cisplatin | Example 5 | 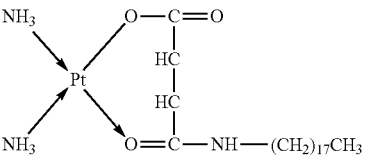 |
| Example 21 | Oxaliplatin | Example 5 | 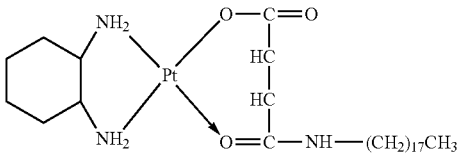 |
| Example 22 | Oxaliplatin | Example 9 | 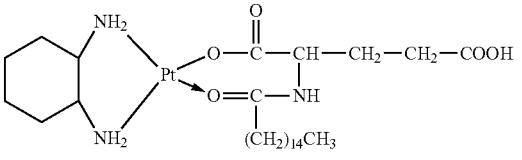 |
| Example 23 | Carboplatin | Example 10 | 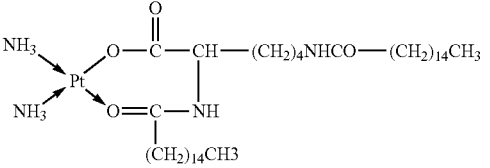 |
| Example 24 | Oxaliplatin | Example 10 | 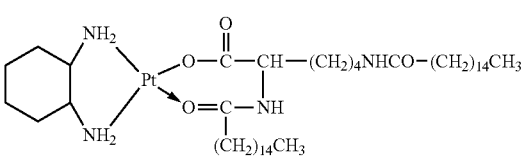 |
| Example 25 | Cisplatin | Example 11 | 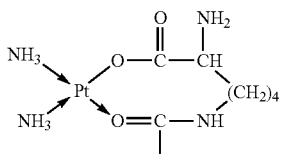 |
| Example 26 | Cisplatin | Chitosan-butanedioic acid | 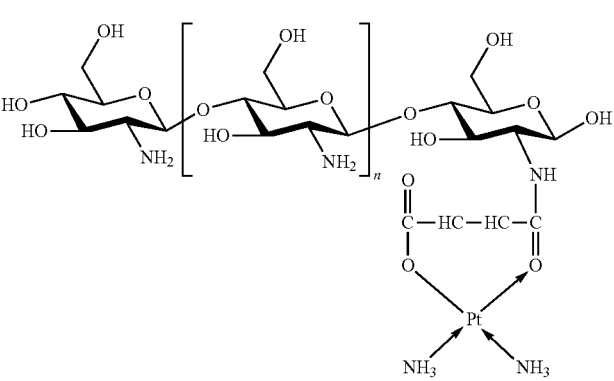 |

TABLE 1-continued

Examples 12-27

| Example No. | Platinum compound | Amphiphilic compound | Prepared platinum complex |
|---|---|---|---|
| Example 27 | Oxaliplatin | Chitosan-butanedioic acid | (structure shown) |

Preparation method: an amphiphilic compound was added to water and stirred to be dissolved under a certain condition. A platinum compound was added (with a molar ratio between the amphiphilic compound and the platinum compound of 1:1-10:1), heated and stirred for 12 h to obtain the platinum complex, which was dried to obtain solid powders of the platinum complex. The powders were subjected to infrared spectrum analysis and the results were shown in FIGS. 2-1a to 2-9b.

The infrared spectrum changed after cisplatin formed a platinum complex with an amphiphilic compound, wherein the vOH peak of the carboxyl group in the amphiphilic compound disappears (3076 cm$^{-1}$), vC=O of the ester bond is shifted from 1720 cm$^{-1}$ to about 1630 cm$^{-1}$-1640 cm$^{-1}$, vC=O of the amide bond is shifted from 1643 cm$^{-1}$ to about 1530 cm$^{-1}$-1570 cm$^{-1}$, and vC—N of cisplatin appears at about 1420-1440 cm$^{-1}$.

The amphiphilic compound forms a complex with oxaliplatin, wherein the vOH peak of the carboxyl group in the amphiphilic compound disappears (3076 cm$^{-1}$, 920 cm$^{-1}$), vC=O of the ester bond is shifted from 1720 cm$^{-1}$ to about 1650 cm$^{-1}$-1700 cm$^{-1}$, vC=O of the amide bond is shifted from 1643 cm$^{-1}$ to about 1530 cm$^{-1}$-1570 cm$^{-1}$, and cyclohexanediamine vs(N—H) of oxaliplatin appears at 3220 cm$^{-1}$ and cyclohexanediamine v(C—N) appears at 1100-1200 cm$^{-1}$.

Examples 28-37: Preparation of Liposomes by Reverse Evaporation

TABLE 2

Examples 28-37

| Example No. | Platinum complex/amount | Membrane material/amount | antioxidant/amount | Long-circulating material/amount | Hydration medium |
|---|---|---|---|---|---|
| 28 | Example 12 complex/equivalent to 7 mg cisplatin | cholesterol/10 mg egg-yolk lecithin/100 mg | VE/5 mg | MPEG2000-DSPE-/2 mg | 0.9% sodium chloride |
| 29 | Example 15 complex/equivalent to 12 mg oxaliplatin | cholesterol/12 mg soy lecithin/120 mg | VE/5 mg | — | 3% mannitol |
| 30 | Example 16 complex/equivalent to 24 mg cisplatin | cholesterol/20 mg hydrogenated soy lecithin/200 mg | VE/10 mg | MPEG2000-DSPE/2 mg | Water for injection |
| 31 | Example 18 complex/equivalent to 12 mg cisplatin | cholesterol/20 mg soy lecithin/200 mg | VE/5 mg | — | Water for injection |
| 32 | Example 19 complex/equivalent to 12 mg oxaliplatin | cholesterol/20 mg soy lecithin/200 mg | VE/5 mg | — | Water for injection |
| 33 | Example 20 complex/equivalent to 24 mg cisplatin | cholesterol/12 mg HSPC/120 mg | VE/5 mg | — | 5% Glucose |
| 34 | Example 22 complex/equivalent to 12 mg cisplatin oxaliplatin | HSPC100 mg DPPG/80 mg | VE/5 mg | — | Water for injection |

TABLE 2-continued

Examples 28-37

| Example No. | Platinum complex/amount | Membrane material/amount | antioxidant/amount | Long-circulating material/amount | Hydration medium |
|---|---|---|---|---|---|
| 35 | Example 23 complex/equivalent to 12 mg carboplatin | soy lecithin/120 mg | VE/5 mg | MPEG2000-DSPE/ 2 mg | Water for injection |
| 36 | Example 25 complex/equivalent to 12 mg cisplatin | Soy phospholipid/80 mg DSPG/40 mg | VE/5 mg | | 2.6% glycerol solution |
| 37 | Example 18 complex/equivalent to 12 mg cisplatin | cholesterol/12 mg soy lecithin/80 mg DSPG/40 mg | –VE/5 mg | MPEG2000-DSPE/ 6 mg | Water for injection |

According to the amounts of a formula, a membrane material and an antioxidant were measured, put into a round-bottom flask and dissolved by adding an appropriate amount of organic solvent (the organic solvent was selected from the group consisting of chloroform or water-saturated ethyl ether or dichloromethane, methanol, ethanol, or a mixed solvent of at least two solvents thereof). A desired amount of the aqueous solution of a platinum complex was added (with a volume ratio of organic solvent:aqueous phase=3:1~6:1), mechanically or ultrasonically homogenized to form a W/O emulsion. The organic solvent was removed by rotary evaporation under reduced pressure, and a thin film was formed on the wall of the container. A hydration medium (physiological saline or 5% glucose or water for injection or aqueous mannitol solution) was added to hydrate the membrane material at 40° C. (or 55° C.) for 1 h-2 h, followed by passing the mixture through a liposome extruder or homogenizing via microfluidics to obtain a platinum complex liposome. A long-circulating material was added and stirred at the room temperature for 1 h.

Example 38: Preparation of Liposomes by Film Dispersion

TABLE 3

Example 38

| Platinum complex/amount | Membrane material/amount | Antioxidant/amount | Long-circulating material/amount | Hydration medium |
|---|---|---|---|---|
| Example 18 complex/equivalent to 18 mg cisplatin | Cholesterol/12 mg soy lecithin/120 mg | VE/5 mg | DSPE-PEG2000/6 mg | Water for injection |

According to the amounts of a formula, a membrane material, an antioxidant and a long-circulating material were measured and put into a round-bottom flask, and a desired amount of a platinum complex was added. The mixture was dissolved by adding an appropriate amount of chloroform. The organic solvent was removed by rotary evaporation under reduced pressure to form a thin film on the wall of the container. A hydration medium (water for injection) was injected to hydrate the membrane material at 40-55° C. for 1 h-2 h, followed by passing through a liposome extruder for homogenization to obtain a novel platinum liposome.

Example 39: Preparation of Liposomes by Double-Emulsion

TABLE 4

Example 39

| Platinum complex/amount | Membrane material/amount | antioxidant/ amount | Long-circulating material/amount | Isotonicity adjusting agent/amoung |
|---|---|---|---|---|
| Example 18 complex/ equivalent to 36 mg cisplatin | Cholesterol 12 mg soy lecithin 120 mg | VE/6 mg | — | Water for injection |

According to the amounts of a formula, a membrane material, and an antioxidant were measured and put into a round-bottom flask, and an appropriate amount of diethyl ether was added for dissolution. A desired amount of a platinum compound aqueous solution (with a volume ratio of organic phase to aqueous phase of 3:1) was added, and ultrasonically or mechanically homogenized to form a W/O emulsion. Part of the organic solvent was removed by rotary evaporation under reduced pressure. Water for injection was injected and mechanically stirred to form W/O/W. The organic solvent was removed by rotary evaporation under reduced pressure, followed by homogenizing through a liposome extruder or via microfluidics, and dispersing to obtain a novel platinum liposome.

Example 40: Liposome Quality Test

The morphology of the platinum complex-containing liposomes obtained according to the present invention was observed by an electron microscope, and the particle size and distribution thereof were measured using a Zetasizer Nano ZS90 laser particle size analyzer. The encapsulation ratio of the liposomes obtained by the present invention was calculated according to the method provided in "Chinese Pharmacopoeia". The results are shown in Table 5:

TABLE 5

Test results of the particle size and encapsulation ratio of liposomes

| Example No. | Mean particle size (nm) | Encapsulation ratio (%) |
| --- | --- | --- |
| 28 | 130.1 | 94.1 |
| 29 | 132.2 | 92.7 |
| 30 | 112.6 | 92.8 |
| 31 | 101.9 | 93.1 |
| 32 | 113.7 | 92.7 |
| 33 | 98.45 | 96.3 |
| 34 | 108.7 | 95.3 |
| 35 | 112.1 | 94.4 |
| 36 | 102.6 | 97.2 |
| 37 | 106.1 | 92.9 |

Figures 2, 3, 3A:
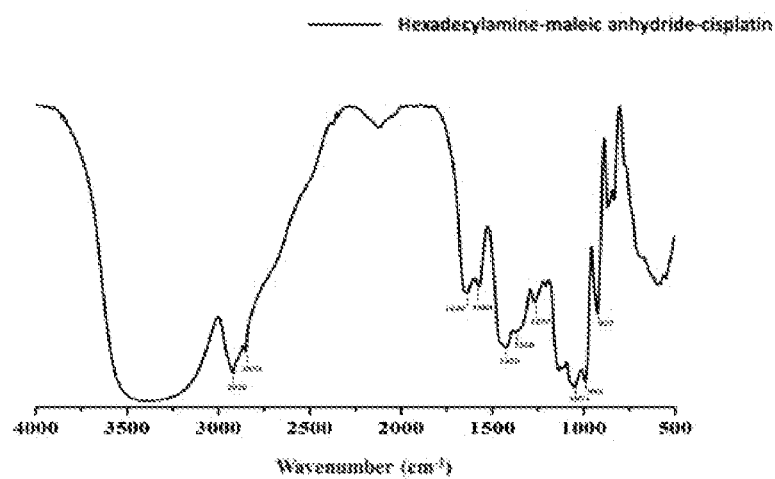
Figures 2, 3, 3B:
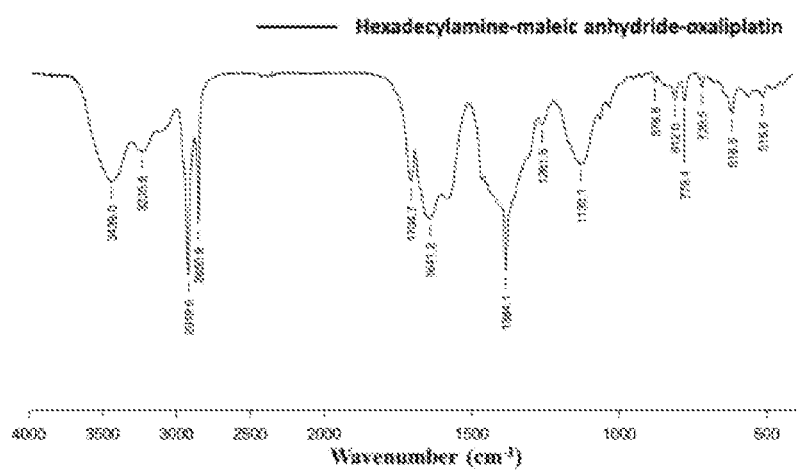
Figures 2, 3, 4, 4A:
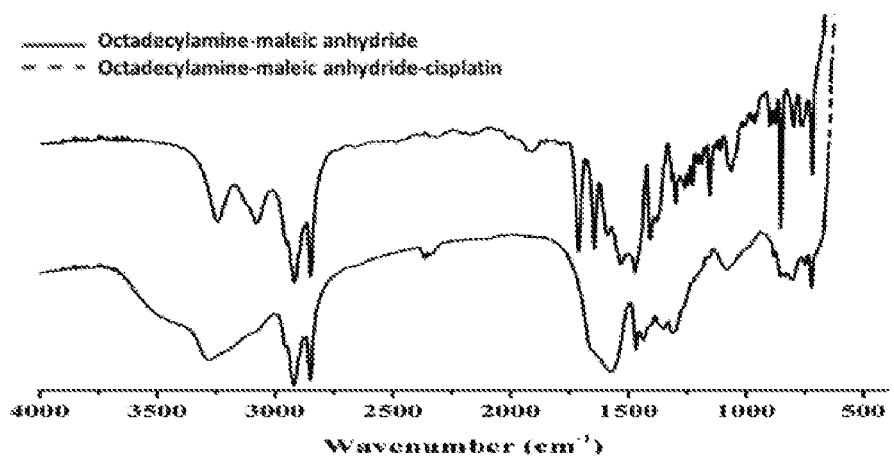
Figures 2, 3, 4, 4B:
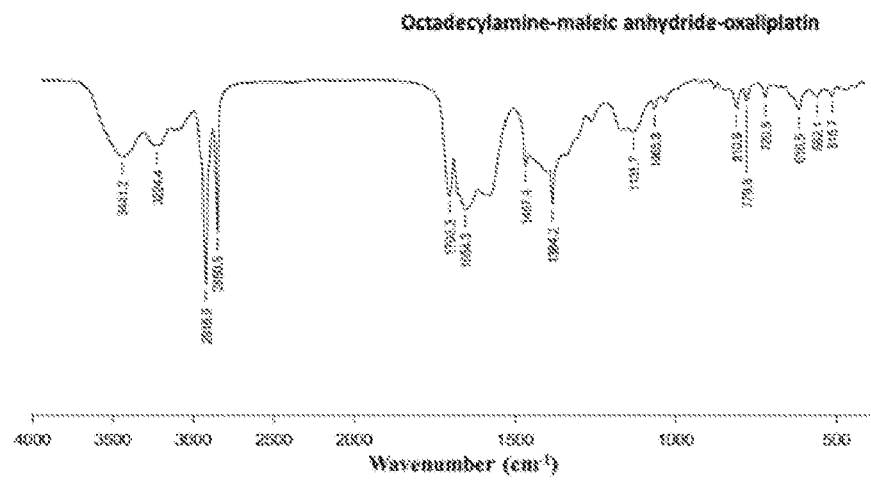

FIGS. 3 and 4 show the morphology and particle size profile of the liposomes obtained in Example 31. Liposomes obtained in other examples are similar thereto.

The results showed that the novel platinum complex liposomes provided by the present invention have a particle size of 90-150 nm, an encapsulation ratio of 92-98%, and a drug loading of 8-30%. Unlike the liposomes reported in the existing literatures and patents, the platinum liposomes have characteristics of a high encapsulation ratio, a good stability and a strong anti-cancer activity.

Example 41: Pharmacodynamics of the Liposomes

1. Cancer Cell Survival Rate and $IC_{50}$

Commercially available cisplatin for injection was used as a control and the liposomes obtained in Examples 31, 33, and 36 were used as experimental materials. MCF-7, A549, and HEPG2 cells in logarithmic phase were digested with trypsin and collected by centrifugation after the digestion was terminated. A cell suspension was prepared and the concentration was adjusted to $5\text{-}10\times10^4$/mL by cell counting. The cell suspension was mixed gently and added to a plate, 100 μL per well. The cells were placed in an incubator and cultured for 24 h. 1 μmol/L, 2 μmol/L, 4 μmol/L, 8 μmol/L, 16 μmol/L, and 32 μmol/L of the cisplatin injection and the liposome solutions obtained in Examples 20-31 were added, respectively. The cells were incubated under 5% $CO_2$ at 37° C. for 48 h. 10 μL MTT solution (5 mg/mL, 0.5% MTT) per cell was added, and the culture was terminated after another 4 h culture. 150 μL of dimethyl sulfoxide per cell was added to each well and the plate was shaken at a low speed shaker for 10 min to fully dissolve the crystals. The absorbance of each well was measured at OD 570 nm by an enzyme-linked immunosorbent assay instrument. $IC_{50}$ values were calculated for each sample according to formula and the results thereof were shown in Table 6.

TABLE 6

$IC_{50}$ (μM) of cisplatin and liposomes obtained in Examples 31, 33 and 36 against different tumor cells

| Example No. | MCF-7 | A549 | HEPG2 |
| --- | --- | --- | --- |
| Cisplatin for injection | 16.9 | 8.92 | 7.19 |
| Example 31 | 3.02 | 1.67 | 1.26 |
| Example 33 | 4.11 | 2.19 | 3.28 |
| Example 36 | 4.22 | 3.97 | 1.19 |

The results show that the liposomes of the platinum complexes provided by the present invention can significantly ($p<0.01$) reduce the $IC_{50}$ value against tumor cells, and the efficacy thereof is significantly improved.

2. Tumor Inhibition Rate

Physiological saline, cisplatin for injection, and liposomes obtained in Examples 31, 33, and 36 were used as experimental materials. Animals for experiments were: SPF-grade KM mice, male, 6-8 weeks old, and weight 18-22 g. Hepatocarcinoma cells $H_{22}$ in logarithmic growth were used and the cell concentration was adjusted to $(1\text{-}5)\times10^6$ cells/mL. The $H_{22}$ cell suspension was inoculated subcutaneously into the right armpit of the mice at 0.2 mL per mouse to establish an underarm inoculation model of the hepatocarcinoma $H_{22}$ cell line. The tumor-bearing mice were randomly divided into 5 groups with 10 per group, respectively: the physiological saline group, the control group of cisplatin for injection, and test groups (given for the platinum complex liposomes provided in Examples 31, 33, and 36 of the present invention, respectively). Intragroup labeling was performed and each group was respectively injected via tail vein with physiological saline. The cisplatin control group and test groups were administered once every fourth day for twice. The dose for administration was 2.5 mg/kg. After administration, the mice were observed daily for survival. The mice were sacrificed on the 7th day after administration, and the tumors thereof were removed. The surface of the tumors was washed with physiological saline, dried with filter paper and weighted to calculate the tumor inhibition rate. The calculation was performed as follows:

Tumor inhibition rate(%)=(mean tumor weight in the control group−mean tumor weight in test group)/mean tumor weight in the control group×100

The experimental results show that the tumor growth of all the administration groups was slower than that of the control group. As compared with the cisplatin control group, the test1 groups significantly inhibited the tumor growth and simultaneously significantly prolonged the survival time of the tumor-bearing mice. Tumor volume and related parameters were shown in Table 7, respectively:

Table 7: Tumor volume and tumor inhibition rate in control group (KM mice bearing hepatocarcinoma $H_{22}$ injected via tail vain with 2.5 mg/kg cisplatin) and experimental groups

| Tumor volume and tumor inhibition rate | | |
| --- | --- | --- |
| Example No. | Tumor weight (g) | Inhibition (%) |
| Physiological saline | 1.220 | |
| Cisplatin injection | 0.661 | 45.8 |
| Example 31 | 0.351 | 71.2 |
| Example 33 | 0.338 | 72.3 |
| Example 36 | 0.403 | 67.0 |

The results show that as compared with the cisplatin injection, the liposomes provided by the present invention can more significantly inhibit tumor growth, and the effect thereof is significantly different from that of the cisplatin injection (p<0.01).

Example 42: Safety of the Liposomes

1. Survival and Weight

KM mice were randomly divided into groups with 5 per group, namely the blank control group, the control group of cisplatin for injection, and liposomes obtained in Examples 31, 33, and 36. Intragroup labeling was performed and each group was injected via tail vein with physiological saline, the commercial cisplatin control and liposomes obtained in Examples 31, 33 and 36 once, respectively. The doses for administration were 10 mg/kg and 20 mg/kg, respectively. After administration, the survival of mice was observed daily, the body weight was measured, and the survival rate was recorded.

Figures 2, 3, 4, 5, 5A:
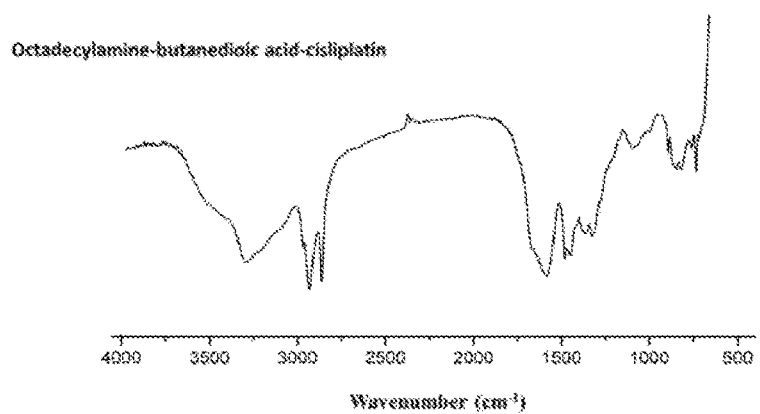
Figures 2, 3, 4, 5, 5B:
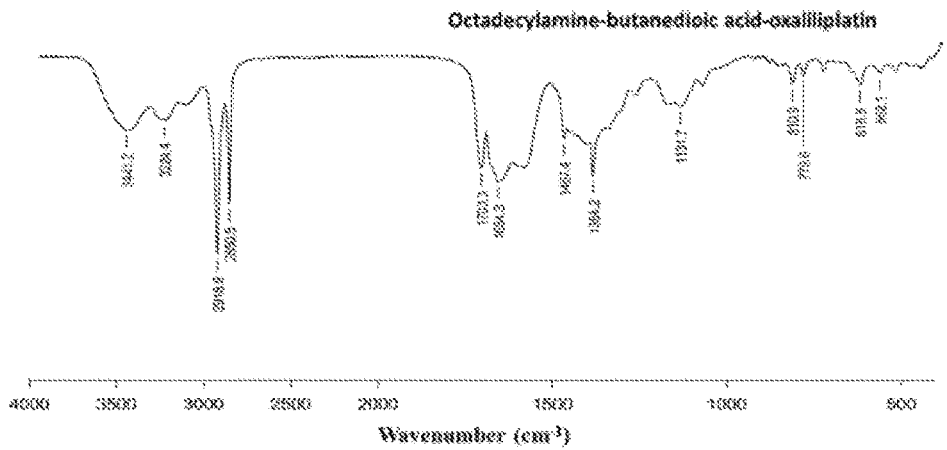
Figures 2, 3, 4, 5, 6, 6A:
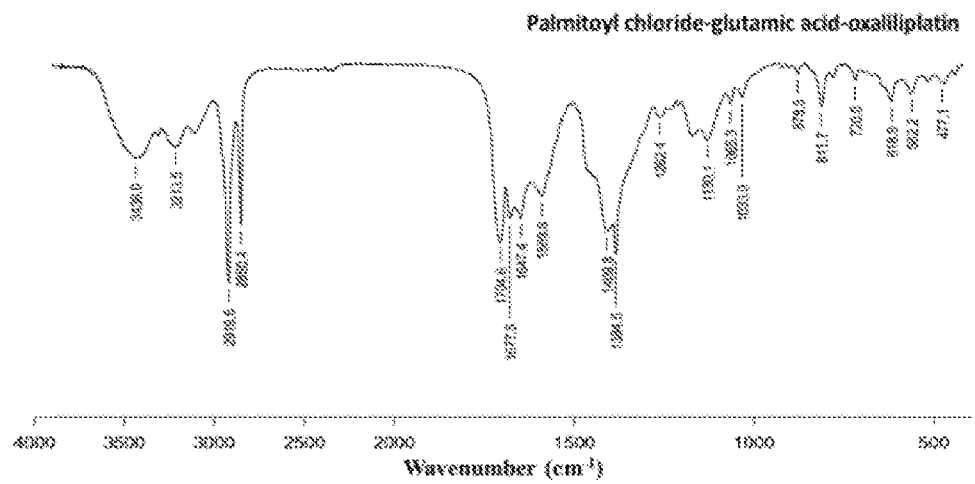
Figures 2, 3, 4, 5, 6, 7, 7A:
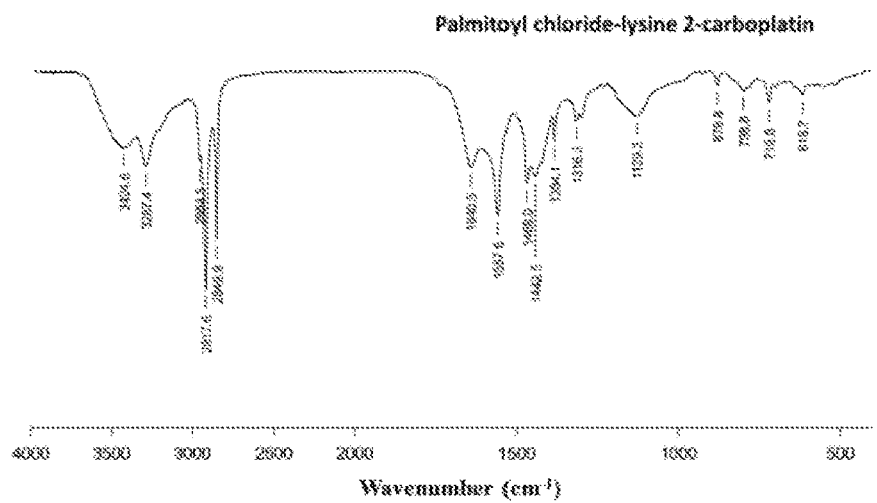
Figures 2, 3, 4, 5, 6, 7, 7B:
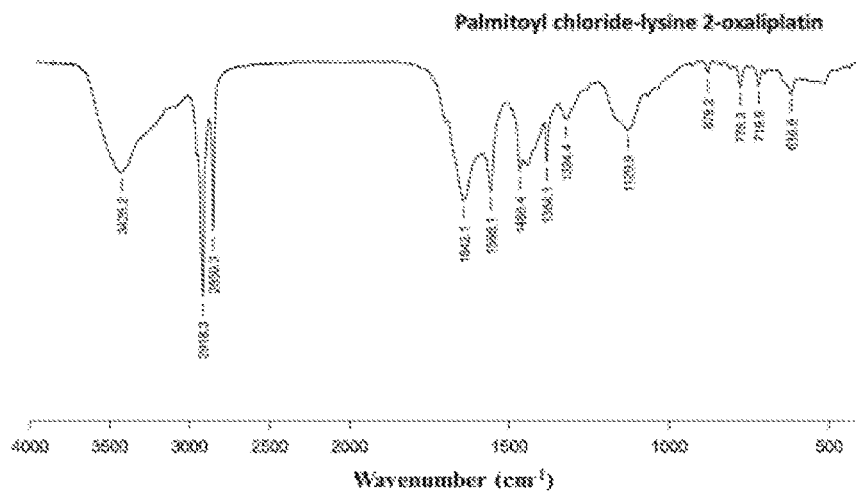
Figures 2, 3, 4, 5, 6, 7, 8, 8A:
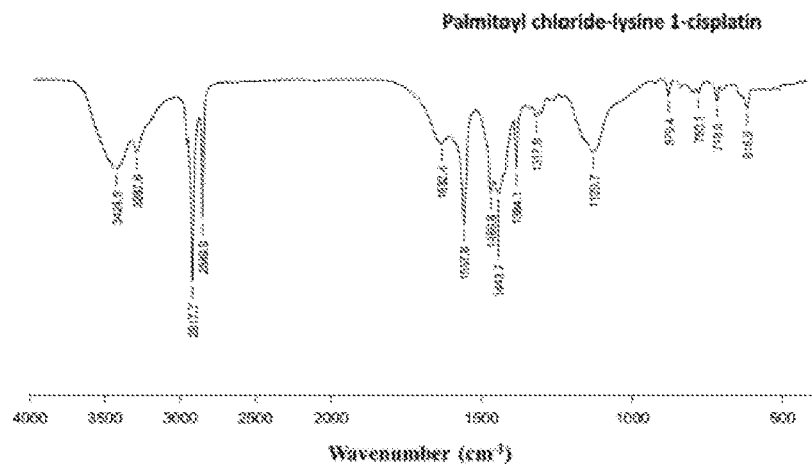
Figures 2, 3, 4, 5, 6, 7, 8, 9, 9A:
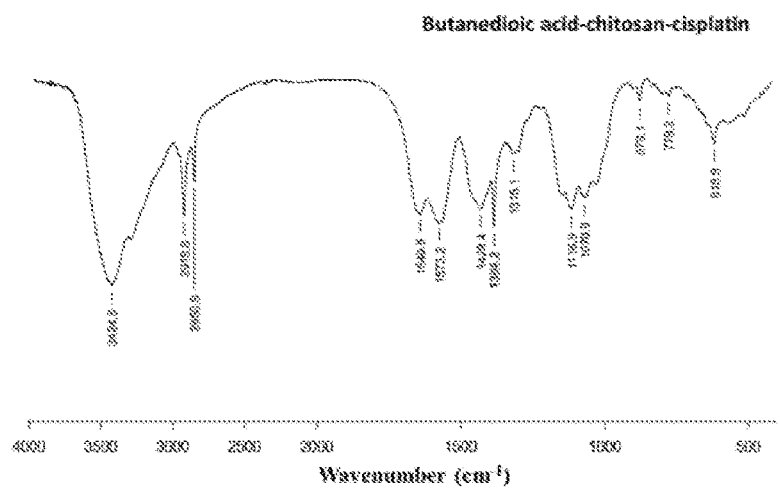
Figures 2, 3, 4, 5, 6, 7, 8, 9, 9B:
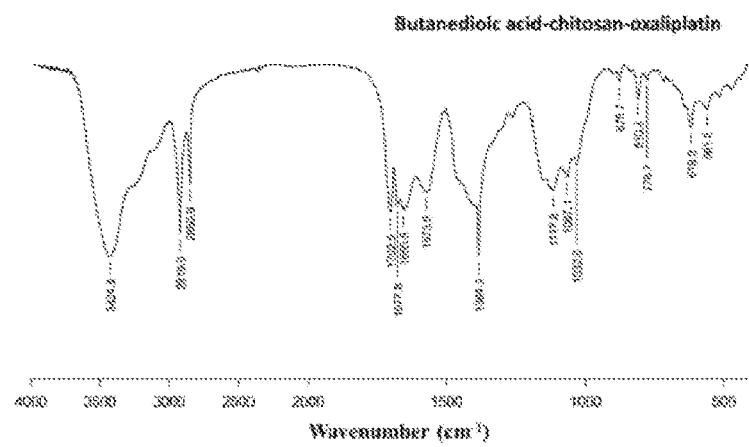
Figure 3:
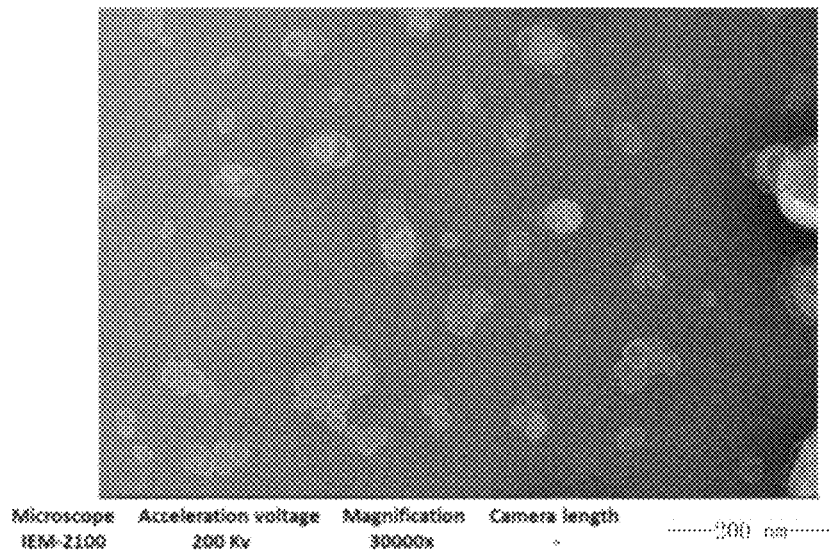
Figure 4:
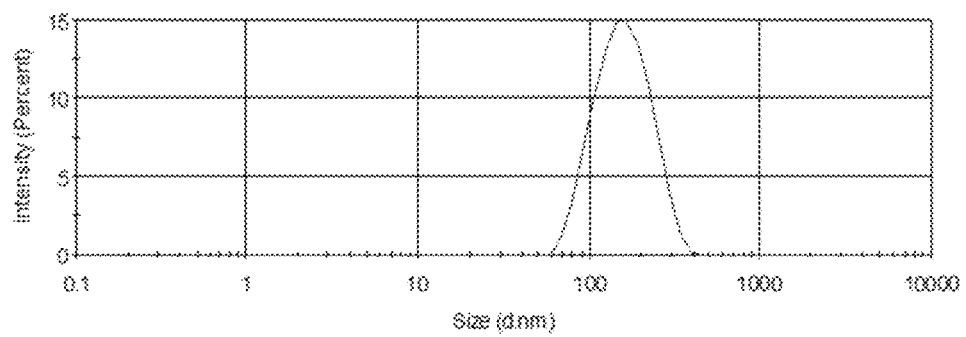
Figure 5:
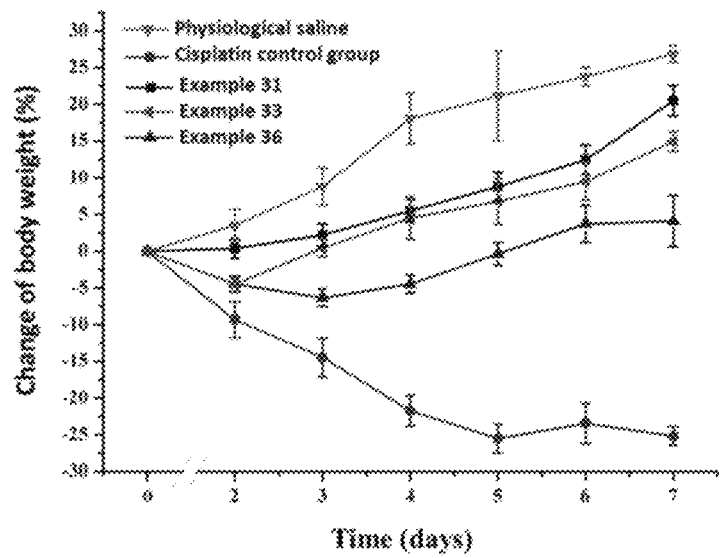
Figure 6:
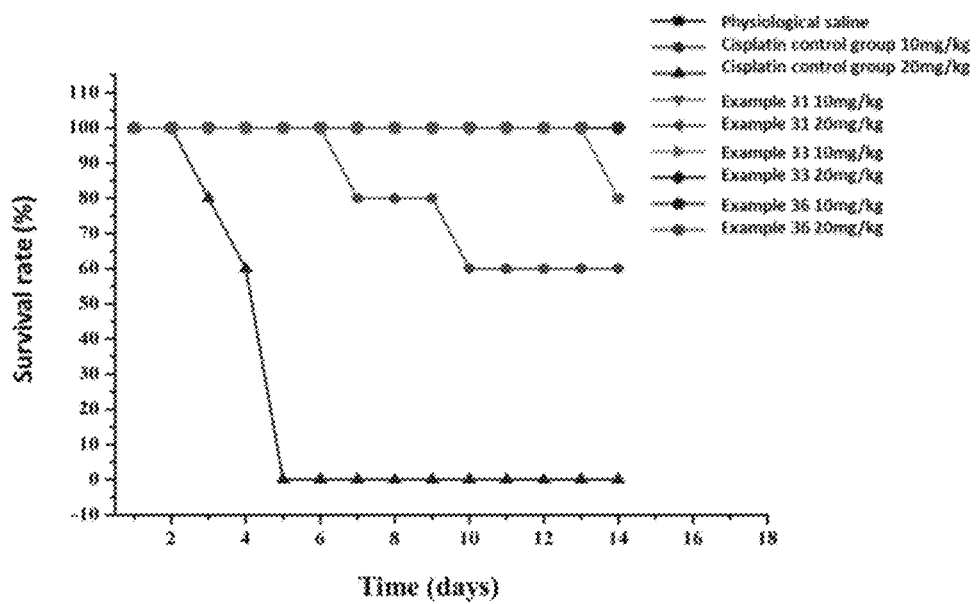

The results were shown in FIGS. 5 and 6. The results show that as compared with the cisplatin control group, the weight loss of the mice was significantly reduced and the survival significantly increased by the liposomes obtained in Examples 31, 33, and 36, indicating that the cisplatin complex liposomes system has a significantly reduced toxicity.

Example 43: Safety of the Liposomes

2. Nephrotoxicity

KM mice were randomly divided into 5 groups with 10 per group, which were the blank control group, liposomes obtained in Examples 31, 33, and 36, and the control group of the commercial cisplatin for injection. Intragroup labeling was performed and each group was injected via tail vein with physiological saline, liposome solutions obtained in Examples 31, 33 and 36, and the cisplatin injection once, respectively. The dose for administration was 10 mg/kg. After administration, the mice were daily observed for survival and sacrificed on the 7th day after administration. The urea nitrogen and creatinine levels were measured in the mice respectively and the results thereof were shown in Table 8.

TABLE 8

| Urea nitrogen and creatinine levels in mice | | |
| --- | --- | --- |
| | Creatinine level ($\mu$mol · L$^{-1}$) | Urea nitrogen (mmol · L$^{-1}$) |
| Physiological saline | 69.66 ± 16.38 | 8.77 ± 1.68 |
| Cisplatin for injection | 134.96 ± 26.24 | 13.49 ± 0.85 |
| Example 31 | 74.25 ± 21.22 | 8.65 ± 0.90 |
| Example 33 | 77.82 ± 27.47 | 7.95 ± 1.23 |
| Example 36 | 68.82 ± 15.47 | 8.85 ± 1.19 |

The experimental results show that the cisplatin complex liposomes obtained in the present invention can significantly reduce the nephrotoxicity of cisplatin as compared with the cisplatin injection.

The above are merely preferred embodiments of the present invention. It should be pointed out that those of ordinary skill in the art can also make several improvements and modifications without departing from the principle of the present invention, and these improvements and modifications should also be regarded as the scope of protection of the present invention.

The invention claimed is:
1. A platinum complex, having a structure represented by formulas I-a to I-d:

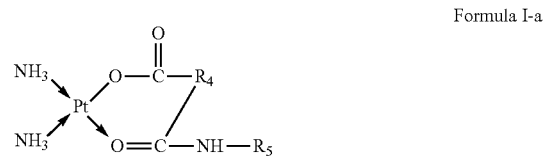

Formula I-a

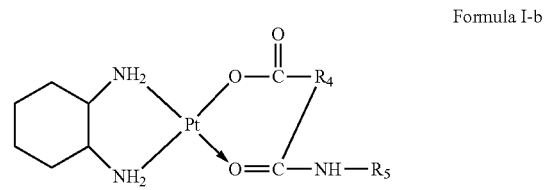

Formula I-b

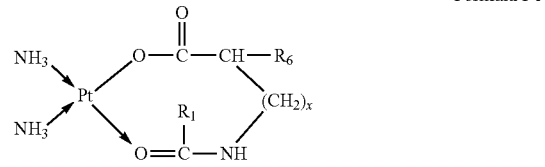

Formula I-c

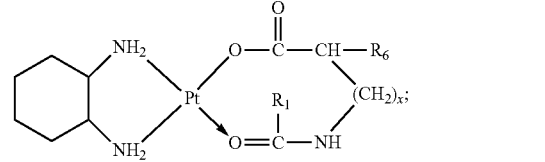

Formula I-d wherein,
$R_1$ is selected from the group consisting of —H, —$C_nH_{2n+1}$, —$C_nH_{2n-1}$, —Ar—$C_nH_{2n+1}$, —Ar—$C_nH_{2n-1}$, —Ar—O—$C_nH_{2n+1}$, and —Ar—O—$C_nH_{2n-1}$, with n=1~22;

$R_4$ is selected from the group consisting of —$C_bH_{2b}$—, —$C_bH_{2b-2}$—, —Ar—$C_bH_{2b-1}$, —Ar—$C_bH_{2b-2}$—, —Ar—O—$C_bH_{2b-1}$, —Ar—O—$C_bH_{2b-2}$—, and hyaluronic acid with two carboxyl groups removed, with b=0~22;

$R_5$ is selected from the group consisting of —H, —$C_cH_{2c+1}$, —$C_cH_{2c-1}$, —Ar—$C_cH_{2c+1}$, —Ar—$CH_{2c-1}$, —Ar—O—$C_cH_{2c+1}$, —Ar—O—$C_cH_{2c-1}$, and chitosan with one amino group removed, with c=1~22;

$R_6$ is selected from the group consisting of —$NH_2$, —NH—CO—$(CH_2)_eCH_3$, —$C_dH_{2d}$—$NH_2$, —$C_dH_{2d-2}$—$NH_2$, —$C_dH_{2d}$—COOH, —$C_dH_{2d-2}$—COOH, and —$C_dH_{2d}$—NH—CO—$(CH_2)_eCH_3$, with d=1~8 and e=1~21;

x=0~10;

wherein H attached to any C can be substituted with a substituent; and wherein the substituent is one or more selected from the group consisting of —$NH_2$, —OH, —COOH, halogen, and —Ar.

2. The platinum complex according to claim 1, wherein:

x=0~10;

$R_1$ is selected from the group consisting of —H, —$C_nH_{2n+1}$, and —$C_nH_{2n-1}$, with n=8~20;

$R_4$ is selected from the group consisting of —$C_bH_{2b}$—, —$C_bH_{2b-2}$—, and hyaluronic acid with two carboxyl groups removed, with b=1~10;

$R_5$ is selected from the group consisting of —$C_cH_{2c+1}$, —$C_cH_{2c-1}$, and chitosan with one amino group removed, with c=8~20; and $R_6$ is selected from the group consisting of —$NH_2$, —NH—CO—$(CH_2)_eCH_3$, —$C_dH_{2d}$—$NH_2$, —$C_dH_{2d}$—COOH, and —$(CH_2)_d$NH—CO—$(CH_2)_eCH_3$, with d=1~6 and e=8~20.

3. The platinum complex according to claim 1, wherein: x=0; $R_1$ is —$C_nH_{2n+1}$, with n=8~18; and $R_6$ is —$(CH_2)_2$COOH, —$CH_2$—COOH, —$(CH_2)_4NH_2$, or —$(CH_2)_4$NH—CO—$(CH_2)_{14}CH_3$.

4. The platinum complex according to claim 1, wherein: x=1~6; $R_1$ is —$C_nH_{2n+1}$, with n=8~18; and $R_6$ is —$NH_2$.

5. The platinum complex according to claim 1, wherein: $R_4$ is selected from the group consisting of —$CH_2$—,

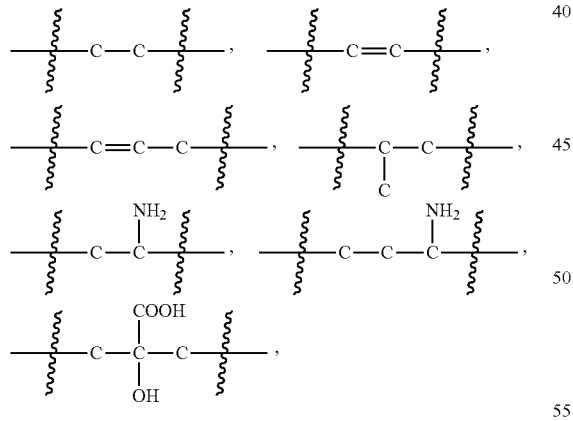

and hyaluronic acid with two carboxyl groups removed; and $R_5$ is —$C_cH_{2c+1}$, with c=12~18.

6. The platinum complex according to claim 1, having a structure represented by formulas (1)-(22), with y=7~17:

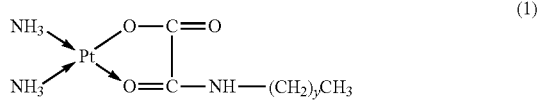
(1)

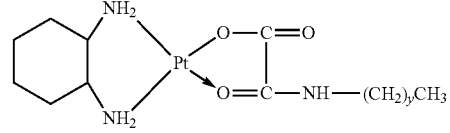
(2)

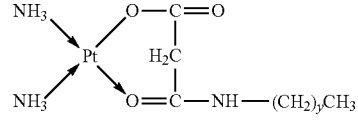
(3)

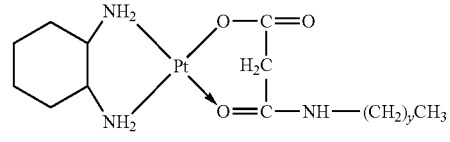
(4)

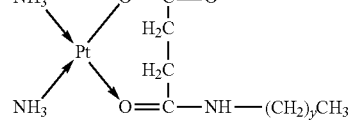
(5)

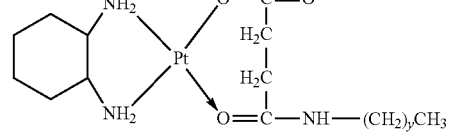
(6)

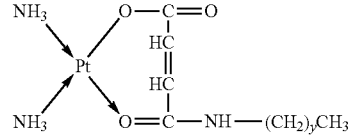
(7)

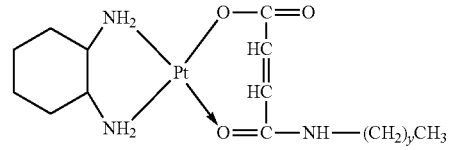
(8)

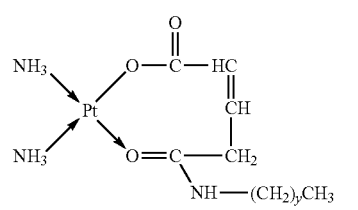
(9)

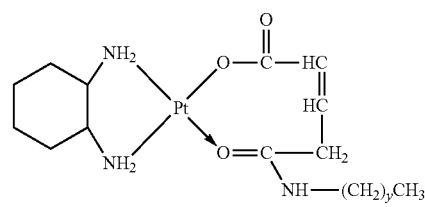
(10)

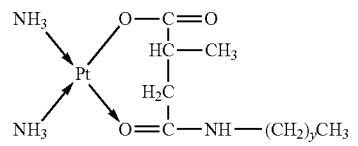
(11)

(12)
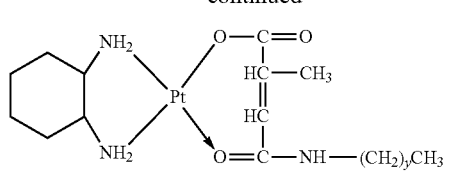
(13)
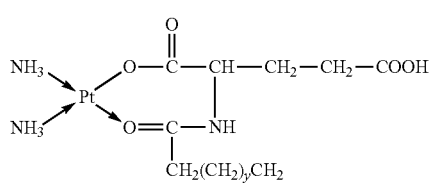
(14)
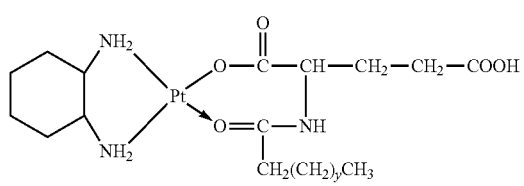
(15)
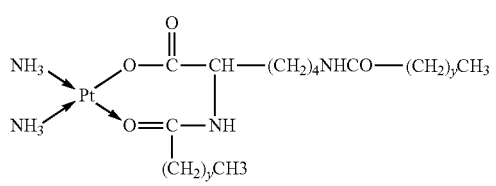
(16)
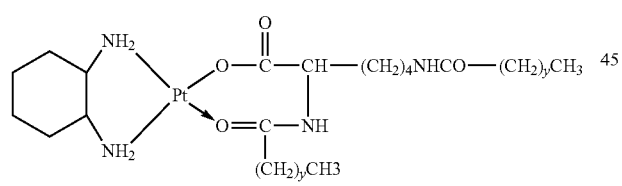
(17)
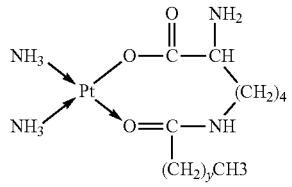
(18)
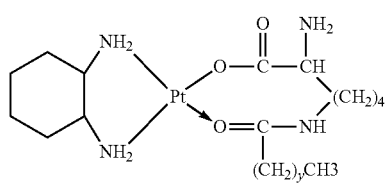
(19)
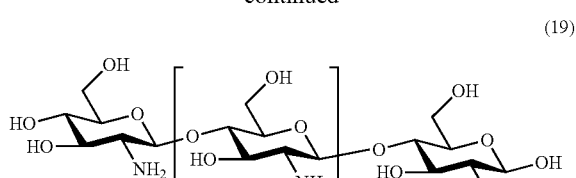
(20)
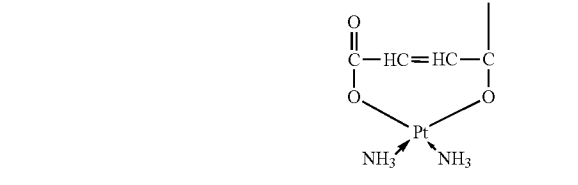
(21)
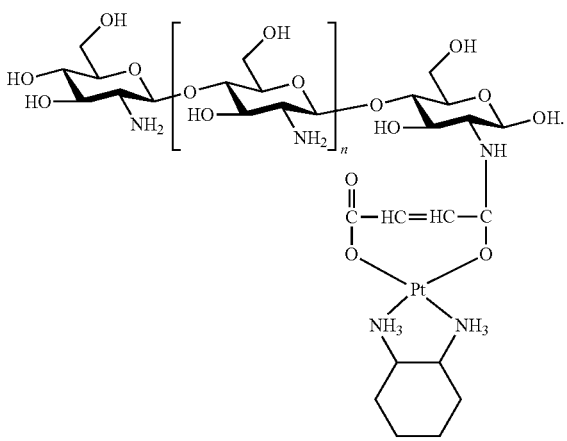
(22)
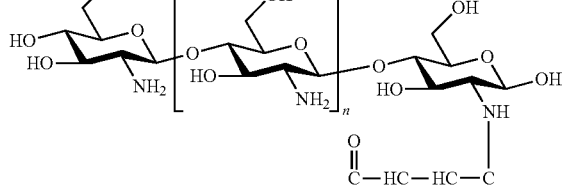
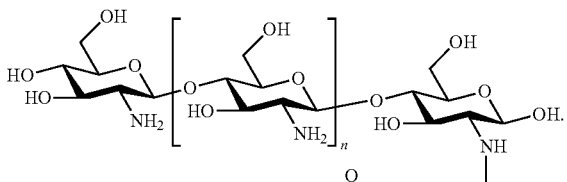

7. The platinum complex according to claim 1, which is in the form of a platinum complex liposome, comprising the platinum complex, a lipid membrane material and/or a stabilizer, wherein the ratio between the platinum complex and the lipid membrane material is (99:1) to (1:99), wherein the ratio is on a mass, molar or volume basis.

8. The liposome according to claim 7, wherein the lipid membrane material comprises a composition of phospholipid and/or cholesterol, wherein the lipid membrane material comprises 1-100 parts phospholipid and 0-60 parts cholesterol by mass.

9. The liposome according to claim 8, wherein the phospholipid is one or a composition of two or more of egg-yolk lecithin, soy lecithin, hydrogenated soya phospholipid, phosphatidylserine, phosphatidylinositol, phosphatidylethanolamine, phosphatidylglycerol, dilauroylphosphatidylcholine, dimyristoyl phosphatidylcholine, dipalmitoylphosphatidylcholine, distearoyl, phosphatidylcholine dioleoylphosphatidylcholine, dilauroylphosphatidylglycerol, dimyristoylphosphatidylglycerol, dipalmitoylphosphatidylglycerol, distearoylphosphatidylglycerol, dioleoylphosphatidylglycerol, phosphoglycerol, dierucoylphosphatidylglycerol, and PEGylated phospholipid.

10. A medicament for the treatment of cancers, comprising the liposome according to claim 7.

* * * * *

UNITED STATES PATENT AND TRADEMARK OFFICE
CERTIFICATE OF CORRECTION

PATENT NO.         : 10,730,898 B2
APPLICATION NO.    : 16/072614
DATED              : August 4, 2020
INVENTOR(S)        : Li Yang et al.

It is certified that error appears in the above-identified patent and that said Letters Patent is hereby corrected as shown below:

In the Claims

Claim 1, Column 36, Lines 29-57, delete the entire contents and insert

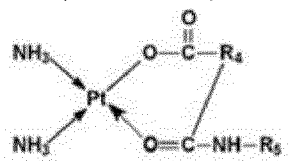
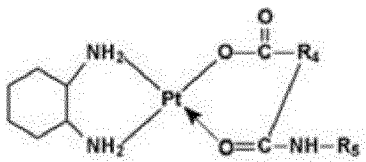

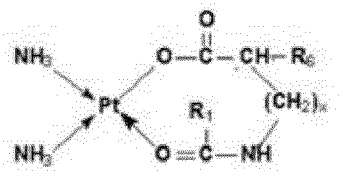
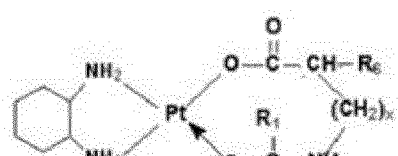

-- therefor.

Claim 1, Column 36, Line 64, delete "-Ar-$C_bH2_{b-1}$," and insert -- -Ar-$C_bH_{2b}$-,-- therefor.

Claim 1, Column 36, Line 65, delete "-Ar-O-$C_bH2_{b-1}$," and insert -- -Ar-O-$C_bH_{2b}$-,-- therefor.

Claim 1, Column 37, Line 2, delete "-Ar-$CH_{2c-1}$," and insert -- -Ar-$C_cH_{2c-1}$,-- therefor.

Claim 6, Column 37, Line 26, through Column 40, Line 65, delete the entire contents of and insert
--6. The platinum complex according to claim 1, having a structure represented by formulas (1)-(22), with y=7~17:

Signed and Sealed this
Twenty-second Day of September, 2020

Andrei Iancu
*Director of the United States Patent and Trademark Office*

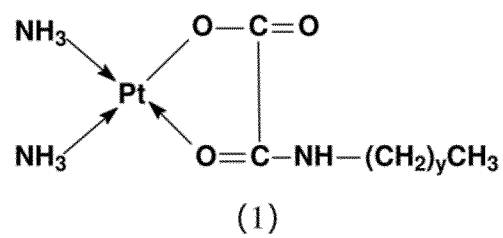
(1)
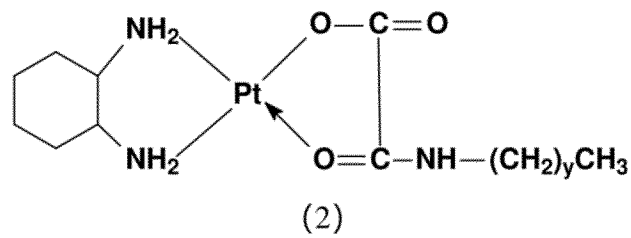
(2)
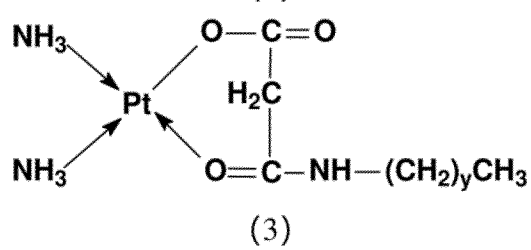
(3)
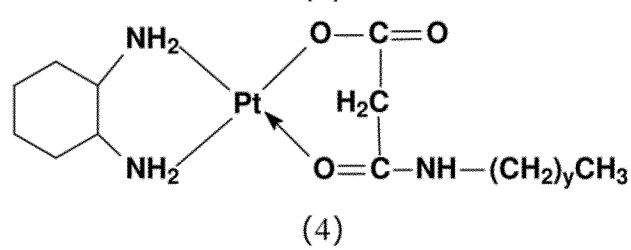
(4)
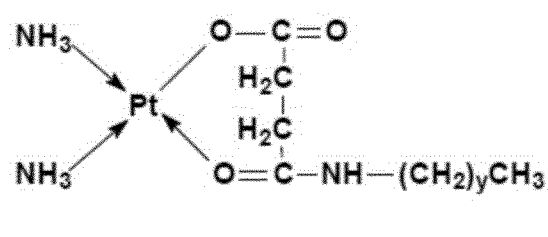
(5)
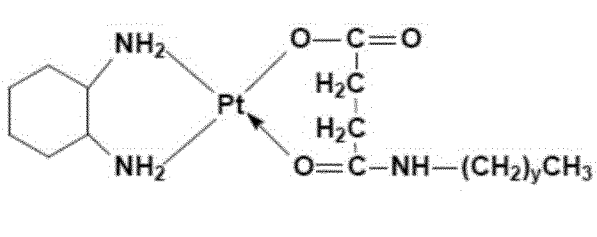
(6)
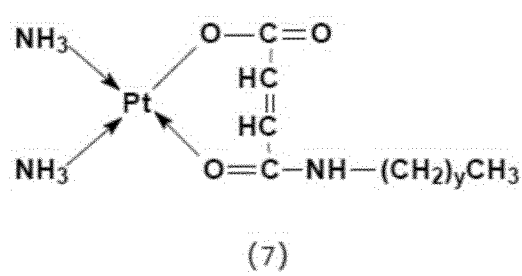
(7)
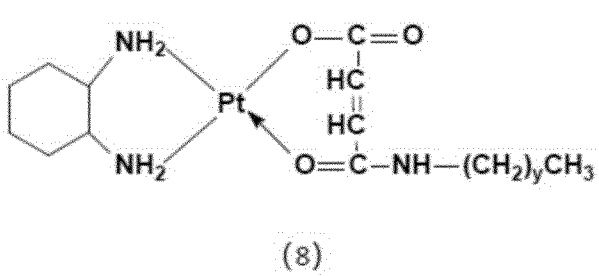
(8)
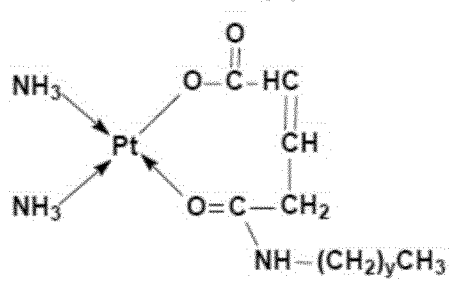
(9)
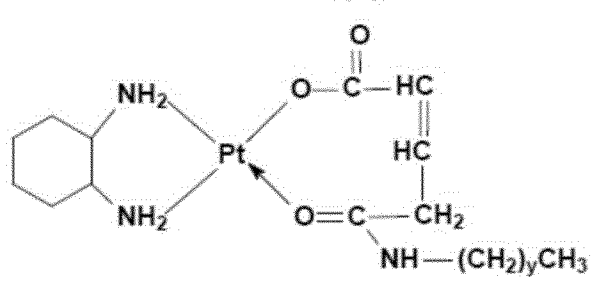
(10)

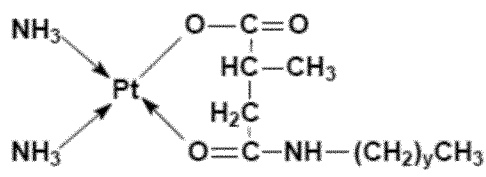
(11)
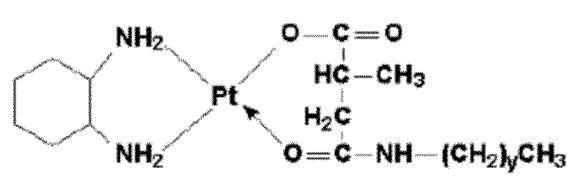
(12)
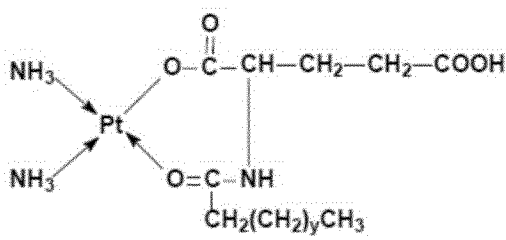
(13)
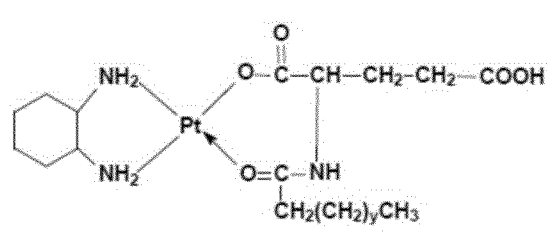
(14)
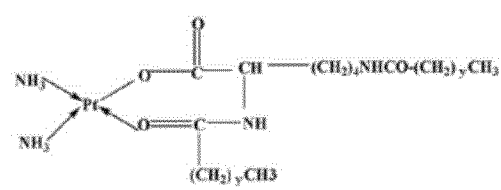
(15)
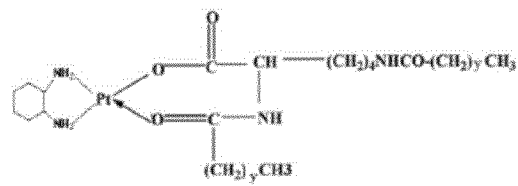
(16)
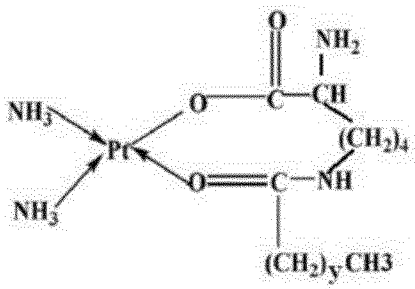
(17)
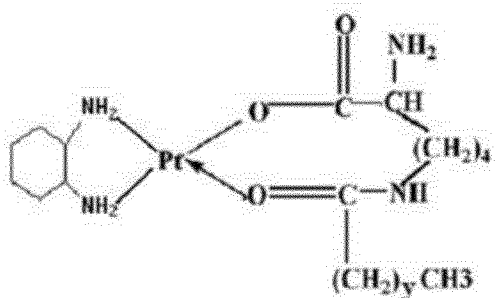
(18)

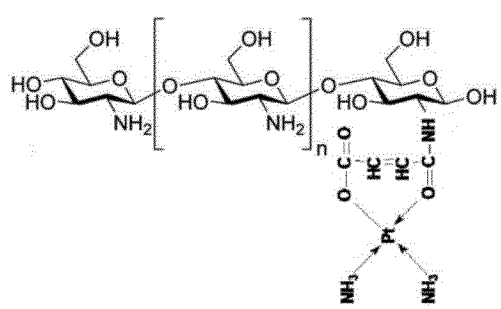
(19)
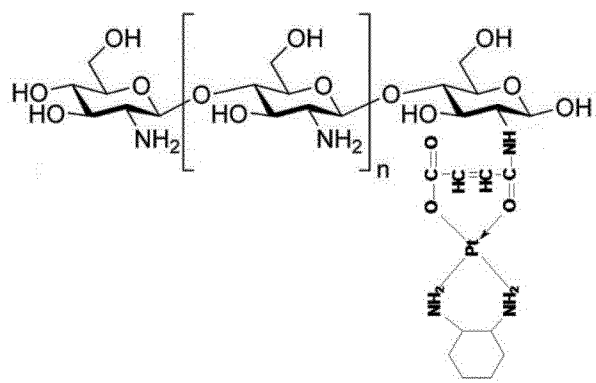
(20)
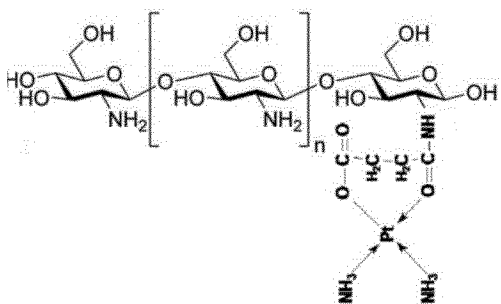
(21)
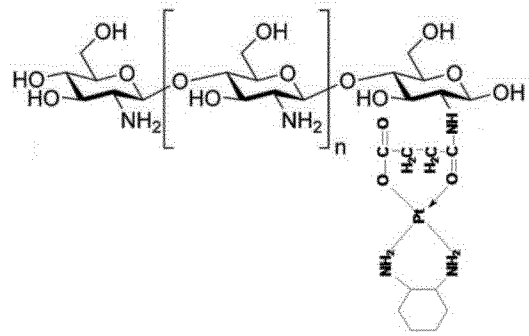
(22) .   --
therefor.